US012653514B2

(12) United States Patent
Hall et al.

(10) Patent No.: US 12,653,514 B2
(45) Date of Patent: Jun. 16, 2026

(54) SECURING A GUIDEWIRE DELIVERY CATHETER IN THE CORONARY SINUS USING A MECHANICALLY RELEASING ARM

(71) Applicant: EDWARDS LIFESCIENCES CORPORATION, Irvine, CA (US)

(72) Inventors: Bethany Jo Hall, Newport Beach, CA (US); Cooper Ryan Rickerson, Huntington Beach, CA (US); Jason James Raid Haddad, Corona, CA (US); Steven Charles Coutteau, Ferndale, MI (US)

(73) Assignee: Edwards Lifesciences Corporation, Irvine, CA (US)

( * ) Notice: Subject to any disclaimer, the term of this patent is extended or adjusted under 35 U.S.C. 154(b) by 247 days.

(21) Appl. No.: 18/513,113

(22) Filed: Nov. 17, 2023

(65) Prior Publication Data

US 2024/0081797 A1 Mar. 14, 2024

Related U.S. Application Data

(63) Continuation of application No. PCT/US2022/030195, filed on May 20, 2022.

(Continued)

(51) Int. Cl.
*A61B 17/00* (2006.01)

(52) U.S. Cl.
CPC .................. *A61B 17/00234* (2013.01); *A61B 2017/00252* (2013.01); *A61B 2017/00867* (2013.01)

(58) Field of Classification Search
CPC .......... A61B 17/00234; A61B 17/3478; A61B 2017/00252; A61B 2017/00867;

(Continued)

(56) References Cited

U.S. PATENT DOCUMENTS 3,538,917 A 11/1970 Selker
3,675,656 A 7/1972 Hakim
(Continued)

FOREIGN PATENT DOCUMENTS

CN 111317516 A 6/2020
CN 113367839 A 9/2021
(Continued)

OTHER PUBLICATIONS

Emil Mantini, MD, et al., Title: Congenital Anomalies Involving the Coronary Sinus, Circulation, Journal of the American Heart Association, vol. XXXIII, Feb. 1966, pp. 317-327.
(Continued)

*Primary Examiner* — Mohamed G Gabr
(74) *Attorney, Agent, or Firm* — Chang and Hale LLP

(57) ABSTRACT

Mechanisms are disclosed for securing a catheter in place to facilitate puncturing a hole through a vessel wall. The securing mechanisms include mechanically releasing arms that press against the wall of the vessel. The mechanically releasing arms are advanced out of the catheter. Outside of the catheter, the securing mechanisms angle or curve toward the vessel wall to contact the wall. The more the mechanically releasing arms are advanced, the closer the approach to the wall and the more force placed against the wall to anchor the catheter in place. The mechanically releasing arms include a plurality of wires that angle or curve toward the vessel wall when deployed, one or more wires that coil away from the catheter to contact the vessel wall when deployed, or a stopper arm with a curved endcap that contacts the vessel wall when deployed.

19 Claims, 6 Drawing Sheets

Related U.S. Application Data

(60) Provisional application No. 63/191,419, filed on May 21, 2021.

(58) Field of Classification Search
CPC .......... A61B 2017/22069; A61B 2017/22071; A61M 25/04
See application file for complete search history.

(56) References Cited

U.S. PATENT DOCUMENTS

| | | | |
|---|---|---|---|
| 3,730,186 A | 5/1973 | Edmunds, Jr. et al. |
| 3,853,126 A | 12/1974 | Schulte |
| 3,882,862 A | 5/1975 | Berend |
| 3,882,882 A | 5/1975 | Preisig |
| 3,903,894 A | 9/1975 | Rosen et al. |
| 4,256,094 A | 3/1981 | Kapp et al. |
| 4,428,365 A | 1/1984 | Hakky |
| 4,556,050 A | 12/1985 | Hodgson et al. |
| 4,578,061 A | 3/1986 | Lemelson |
| 4,586,501 A | 5/1986 | Claracq |
| 4,601,718 A | 7/1986 | Possis et al. |
| 4,655,777 A | 4/1987 | Dunn et al. |
| 4,708,140 A | 11/1987 | Baron |
| 4,712,551 A | 12/1987 | Rayhanabad |
| 4,739,762 A | 4/1988 | Palmaz |
| 4,762,128 A | 8/1988 | Rosenbluth |
| 4,774,949 A | 10/1988 | Fogarty |
| 4,828,544 A | 5/1989 | Lane et al. |
| 4,861,336 A | 8/1989 | Helzel |
| 4,881,939 A | 11/1989 | Newman |
| 4,946,457 A | 8/1990 | Elliott |
| 4,950,227 A | 8/1990 | Savin et al. |
| 4,961,729 A | 10/1990 | Vaillancourt |
| 4,997,431 A | 3/1991 | Isner et al. |
| 5,026,377 A | 6/1991 | Burton et al. |
| 5,054,492 A | 10/1991 | Scribner et al. |
| 5,108,420 A | 4/1992 | Marks |
| 5,109,420 A | 4/1992 | Nonaka |
| 5,114,408 A | 5/1992 | Fleischhaker et al. |
| 5,167,239 A | 12/1992 | Cohen et al. |
| 5,190,528 A | 3/1993 | Fonger et al. |
| 5,193,546 A | 3/1993 | Shaknovich |
| 5,201,757 A | 4/1993 | Heyn et al. |
| 5,242,397 A | 9/1993 | Barath et al. |
| 5,242,410 A | 9/1993 | Melker |
| 5,256,146 A | 10/1993 | Ensminger et al. |
| 5,258,042 A | 11/1993 | Mehta |
| 5,267,940 A | 12/1993 | Moulder |
| 5,287,861 A | 2/1994 | Wilk |
| 5,320,613 A | 6/1994 | Houge et al. |
| 5,330,496 A | 7/1994 | Alferness |
| 5,334,217 A | 8/1994 | Das |
| 5,345,940 A | 9/1994 | Seward et al. |
| 5,354,279 A | 10/1994 | Hofling |
| 5,366,490 A | 11/1994 | Edwards et al. |
| 5,373,849 A | 12/1994 | Maroney et al. |
| 5,419,777 A | 5/1995 | Hofling |
| 5,423,878 A | 6/1995 | Franz |
| 5,429,634 A | 7/1995 | Narciso, Jr. |
| 5,431,700 A | 7/1995 | Sloan |
| 5,443,497 A | 8/1995 | Venbrux |
| 5,445,600 A | 8/1995 | Abdulla |
| 5,445,646 A | 8/1995 | Euteneuer et al. |
| 5,456,284 A | 10/1995 | Ryan et al. |
| 5,456,712 A | 10/1995 | Maginot |
| 5,462,523 A | 10/1995 | Samson et al. |
| 5,464,395 A | 11/1995 | Faxon et al. |
| 5,491,224 A | 2/1996 | Bittner et al. |
| 5,492,304 A | 2/1996 | Smith et al. |
| 5,496,311 A | 3/1996 | Abele et al. |
| 5,499,630 A | 3/1996 | Hiki et al. |
| 5,507,724 A | 4/1996 | Hofmann et al. |
| 5,507,725 A | 4/1996 | Savage et al. |
| 5,538,504 A | 7/1996 | Linden et al. |
| 5,551,954 A | 9/1996 | Buscemi et al. |
| 5,554,182 A | 9/1996 | Dinh et al. |
| 5,570,693 A | 11/1996 | Jang et al. |
| 5,571,086 A | 11/1996 | Kaplan et al. |
| 5,571,151 A | 11/1996 | Gregory |
| 5,588,960 A | 12/1996 | Edwards et al. |
| 5,597,146 A | 1/1997 | Putman |
| 5,597,378 A | 1/1997 | Jervis |
| 5,599,300 A | 2/1997 | Weaver et al. |
| 5,614,204 A | 3/1997 | Cochrum |
| 5,628,784 A | 5/1997 | Strecker |
| 5,661,133 A | 8/1997 | Leiden et al. |
| 5,662,609 A | 9/1997 | Slepian |
| 5,662,711 A | 9/1997 | Douglas |
| 5,665,077 A | 9/1997 | Rosen et al. |
| 5,669,880 A | 9/1997 | Solar |
| 5,682,906 A | 11/1997 | Sterman et al. |
| 5,690,670 A | 11/1997 | Davidson |
| 5,693,029 A | 12/1997 | Leonhardt |
| 5,704,361 A | 1/1998 | Seward et al. |
| 5,704,926 A | 1/1998 | Sutton |
| 5,713,363 A | 2/1998 | Seward et al. |
| 5,713,853 A | 2/1998 | Clark et al. |
| 5,718,725 A | 2/1998 | Sterman et al. |
| 5,724,975 A | 3/1998 | Negus et al. |
| 5,724,977 A | 3/1998 | Yock et al. |
| 5,728,123 A | 3/1998 | Lemelson et al. |
| 5,735,847 A | 4/1998 | Gough et al. |
| 5,738,658 A | 4/1998 | Maus et al. |
| 5,743,874 A | 4/1998 | Fischell et al. |
| 5,755,682 A | 5/1998 | Knudson et al. |
| 5,756,696 A | 5/1998 | Gray et al. |
| 5,771,895 A | 6/1998 | Slager |
| 5,772,629 A | 6/1998 | Kaplan |
| 5,772,632 A | 6/1998 | Forman |
| 5,807,258 A | 9/1998 | Cimochowski et al. |
| 5,807,306 A | 9/1998 | Shapland et al. |
| 5,810,780 A | 9/1998 | Brimhall et al. |
| 5,814,005 A | 9/1998 | Barra et al. |
| 5,827,216 A | 10/1998 | Igo et al. |
| 5,830,222 A | 11/1998 | Makower |
| 5,830,224 A | 11/1998 | Cohn et al. |
| 5,836,913 A | 11/1998 | Orth et al. |
| 5,843,090 A | 12/1998 | Schuetz |
| 5,843,170 A | 12/1998 | Ahn |
| 5,944,738 A | 8/1999 | Amplatz et al. |
| 5,951,569 A | 9/1999 | Tuckey et al. |
| 5,954,691 A | 9/1999 | Prosl |
| 5,989,280 A | 11/1999 | Euteneuer et al. |
| 6,019,788 A | 2/2000 | Butters et al. |
| 6,042,589 A | 3/2000 | Marianne |
| 6,053,891 A | 4/2000 | DeCampli |
| 6,081,738 A | 6/2000 | Hinohara et al. |
| 6,086,553 A | 7/2000 | Akbik |
| 6,092,526 A | 7/2000 | LaFontaine et al. |
| 6,095,878 A | 8/2000 | Van Balen |
| 6,113,612 A | 9/2000 | Swanson et al. |
| 6,120,494 A | 9/2000 | Jonkman |
| 6,120,522 A | 9/2000 | Vrba et al. |
| 6,120,534 A | 9/2000 | Ruiz |
| 6,152,937 A | 11/2000 | Peterson et al. |
| 6,165,185 A | 12/2000 | Shennib et al. |
| 6,168,620 B1 | 1/2001 | Kerr |
| 6,168,820 B1 | 1/2001 | Garwood et al. |
| 6,174,681 B1 | 1/2001 | Halling et al. |
| 6,190,353 B1 | 2/2001 | Makower et al. |
| 6,193,734 B1 | 2/2001 | Bolduc et al. |
| 6,196,230 B1 | 3/2001 | Hall et al. |
| 6,241,743 B1 | 6/2001 | Levin et al. |
| 6,248,117 B1 | 6/2001 | Blatter |
| 6,251,116 B1 | 6/2001 | Shennib et al. |
| 6,254,631 B1 | 7/2001 | Thompson |
| 6,280,412 B1 | 8/2001 | Pederson, Jr. et al. |
| 6,283,951 B1 | 9/2001 | Flaherty et al. |
| 6,287,280 B1 | 9/2001 | Lampropoulos et al. |
| 6,287,332 B1 | 9/2001 | Bolz et al. |
| 6,290,728 B1 | 9/2001 | Phelps et al. |
| 6,302,875 B1 | 10/2001 | Makower et al. |
| 6,302,892 B1 | 10/2001 | Wilk |
| 6,302,905 B1 | 10/2001 | Goldsteen et al. |

(56)                    References Cited

U.S. PATENT DOCUMENTS

| | | | |
|---|---|---|---|
| 6,309,415 | B1 | 10/2001 | Pulnev et al. |
| 6,315,752 | B1 | 11/2001 | DiMatteo |
| 6,325,798 | B1 | 12/2001 | Edwards et al. |
| 6,361,545 | B1 | 3/2002 | Macoviak et al. |
| 6,375,615 | B1 | 4/2002 | Flaherty et al. |
| 6,387,116 | B1 | 5/2002 | Mckenzie et al. |
| 6,387,119 | B2 | 5/2002 | Wolf et al. |
| 6,391,036 | B1 | 5/2002 | Berg et al. |
| 6,402,767 | B1 | 6/2002 | Nash et al. |
| 6,443,158 | B1 | 9/2002 | LaFontaine et al. |
| 6,451,048 | B1 | 9/2002 | Berg et al. |
| 6,458,140 | B2 | 10/2002 | Akin et al. |
| 6,464,665 | B1 | 10/2002 | Heuser |
| 6,468,303 | B1 | 10/2002 | Amplatz et al. |
| 6,475,226 | B1 | 11/2002 | Belef et al. |
| 6,494,889 | B1 | 12/2002 | Fleischman et al. |
| 6,503,247 | B2 | 1/2003 | Swartz et al. |
| 6,506,201 | B2 | 1/2003 | Di Caprio et al. |
| 6,508,824 | B1 | 1/2003 | Flaherty et al. |
| 6,561,998 | B1 | 5/2003 | Roth et al. |
| 6,562,066 | B1 | 5/2003 | Martin |
| 6,565,542 | B2 | 5/2003 | Kumar et al. |
| 6,575,168 | B2 | 6/2003 | LaFontaine et al. |
| 6,579,311 | B1 | 6/2003 | Makower |
| 6,589,251 | B2 | 7/2003 | Yee et al. |
| 6,595,941 | B1 | 7/2003 | Blatter |
| 6,602,241 | B2 | 8/2003 | Makower et al. |
| 6,613,074 | B1 | 9/2003 | Mitelberg et al. |
| 6,616,624 | B1 | 9/2003 | Kieval |
| 6,616,675 | B1 | 9/2003 | Evard et al. |
| 6,620,202 | B2 | 9/2003 | Bottcher et al. |
| 6,623,494 | B1 | 9/2003 | Blatter |
| 6,626,920 | B2 | 9/2003 | Whayne |
| 6,638,293 | B1 | 10/2003 | Makower et al. |
| 6,645,160 | B1 | 11/2003 | Heesch |
| 6,692,482 | B2 | 2/2004 | Heller et al. |
| 6,695,878 | B2 | 2/2004 | McGuckin, Jr. et al. |
| 6,699,256 | B1 | 3/2004 | Logan et al. |
| 6,702,828 | B2 | 3/2004 | Whayne |
| 6,709,414 | B2 | 3/2004 | Weitzel et al. |
| 6,709,444 | B1 | 3/2004 | Makower |
| 6,712,836 | B1 | 3/2004 | Berg et al. |
| 6,719,804 | B2 | 4/2004 | St. Pierre |
| 6,726,659 | B1 | 4/2004 | Stocking et al. |
| 6,726,677 | B1 | 4/2004 | Flaherty et al. |
| 6,736,825 | B2 | 5/2004 | Blatter et al. |
| 6,740,426 | B2 | 5/2004 | Kawachi et al. |
| 6,743,244 | B2 | 6/2004 | Blatter et al. |
| 6,743,259 | B2 | 6/2004 | Ginn |
| 6,746,426 | B1 | 6/2004 | Flaherty et al. |
| 6,748,484 | B1 | 6/2004 | Henderson et al. |
| 6,758,854 | B1 | 7/2004 | Butler et al. |
| 6,776,785 | B1 | 8/2004 | Yencho et al. |
| 6,797,083 | B2 | 9/2004 | Peterson |
| 6,802,858 | B2 | 10/2004 | Gambale et al. |
| 6,805,706 | B2 | 10/2004 | Solovay et al. |
| 6,808,498 | B2 | 10/2004 | Laroya et al. |
| 6,827,698 | B1 | 12/2004 | Kleinekofort |
| 6,847,348 | B2 | 1/2005 | Rojewski |
| 6,854,172 | B2 | 2/2005 | Kaese et al. |
| 6,858,035 | B2 | 2/2005 | Whayne |
| 6,869,437 | B1 | 3/2005 | Hausen et al. |
| 6,893,413 | B2 | 5/2005 | Martin |
| 6,913,600 | B2 | 7/2005 | Valley et al. |
| 6,913,607 | B2 | 7/2005 | Ainsworth et al. |
| 6,915,154 | B1 | 7/2005 | Docherty et al. |
| 6,926,690 | B2 | 8/2005 | Renati |
| 6,972,023 | B2 | 12/2005 | Whayne et al. |
| 6,979,351 | B2 | 12/2005 | Forsell et al. |
| 6,985,774 | B2 | 1/2006 | Kieval et al. |
| 7,002,491 | B2 | 2/2006 | Robbins |
| 7,008,397 | B2 | 3/2006 | Tweden et al. |
| 7,011,094 | B2 | 3/2006 | Rapacki et al. |
| 7,011,678 | B2 | 3/2006 | Tenerz et al. |
| 7,025,741 | B2 | 4/2006 | Cull |
| 7,025,746 | B2 | 4/2006 | Tal |
| 7,037,329 | B2 | 5/2006 | Martin |
| 7,056,294 | B2 | 6/2006 | Khairkhahan et al. |
| 7,056,320 | B2 | 6/2006 | Utley et al. |
| 7,056,325 | B1 | 6/2006 | Makower et al. |
| 7,077,860 | B2 | 7/2006 | Yan et al. |
| 7,083,631 | B2 | 8/2006 | Houser et al. |
| 7,108,701 | B2 | 9/2006 | Evens et al. |
| 7,115,136 | B2 | 10/2006 | Park et al. |
| 7,118,546 | B2 | 10/2006 | Blatter |
| 7,128,750 | B1 | 10/2006 | Stergiopulos |
| 7,175,644 | B2 | 2/2007 | Cooper et al. |
| 7,182,771 | B1 | 2/2007 | Houser et al. |
| 7,235,095 | B2 | 6/2007 | Haverkost et al. |
| 7,294,115 | B1 | 11/2007 | Wilk |
| 7,316,706 | B2 | 1/2008 | Bloom et al. |
| 7,317,951 | B2 | 1/2008 | Schneider et al. |
| 7,318,804 | B2 | 1/2008 | Weitzel et al. |
| 7,326,221 | B2 | 2/2008 | Sakamoto et al. |
| 7,331,985 | B2 | 2/2008 | Thompson et al. |
| 7,335,220 | B2 | 2/2008 | Khosravi et al. |
| 7,351,247 | B2 | 4/2008 | Kupiecki et al. |
| 7,361,181 | B2 | 4/2008 | Hindrichs et al. |
| 7,374,567 | B2 | 5/2008 | Heuser |
| D581,054 | S | 11/2008 | Moore |
| 7,462,162 | B2 | 12/2008 | Phan et al. |
| 7,476,200 | B2 | 1/2009 | Tal |
| 7,530,963 | B2 | 5/2009 | Albright |
| 7,563,277 | B2 | 7/2009 | Case et al. |
| 7,623,926 | B2 | 11/2009 | Rossing et al. |
| 7,625,593 | B2 | 12/2009 | Mandrusov et al. |
| 7,628,768 | B2 | 12/2009 | Faul et al. |
| D612,499 | S | 3/2010 | Ondracek et al. |
| 7,691,110 | B2 | 4/2010 | Secrest et al. |
| 7,699,863 | B2 | 4/2010 | Marco et al. |
| 7,722,549 | B2 | 5/2010 | Nakao |
| 7,722,665 | B2 | 5/2010 | Anwar et al. |
| 7,744,621 | B2 | 6/2010 | Paul et al. |
| 7,794,495 | B2 | 9/2010 | Gale et al. |
| 7,807,191 | B2 | 10/2010 | Iyer et al. |
| 7,815,590 | B2 | 10/2010 | Cooper |
| 7,815,656 | B2 | 10/2010 | Rust et al. |
| 7,815,852 | B2 | 10/2010 | Sternby |
| 7,828,814 | B2 | 11/2010 | Brenneman et al. |
| 7,846,179 | B2 | 12/2010 | Belef et al. |
| 7,846,194 | B2 | 12/2010 | Hartley et al. |
| 7,850,705 | B2 | 12/2010 | Bachinski et al. |
| 7,867,547 | B2 | 1/2011 | Tochterman et al. |
| 7,879,367 | B2 | 2/2011 | Heublein et al. |
| 7,892,246 | B2 | 2/2011 | Akin et al. |
| 7,892,247 | B2 | 2/2011 | Conston et al. |
| 7,923,022 | B2 | 4/2011 | Wang et al. |
| 7,951,194 | B2 | 5/2011 | Gueriguian et al. |
| 7,959,603 | B2 | 6/2011 | Wahr et al. |
| 7,964,210 | B2 | 6/2011 | Wang et al. |
| 7,967,769 | B2 | 6/2011 | Faul et al. |
| 7,972,346 | B2 | 7/2011 | Bachmann et al. |
| 8,002,821 | B2 | 8/2011 | Stinson |
| 8,016,782 | B2 | 9/2011 | Brenneman et al. |
| 8,029,470 | B2 | 10/2011 | Whiting et al. |
| 8,048,150 | B2 | 11/2011 | Weber et al. |
| 8,052,751 | B2 | 11/2011 | Aklog et al. |
| 8,057,534 | B2 | 11/2011 | Boismier et al. |
| 8,070,708 | B2 | 12/2011 | Rottenberg et al. |
| 8,088,171 | B2 | 1/2012 | Brenneman |
| 8,089,029 | B2 | 1/2012 | Flanagan |
| 8,091,556 | B2 | 1/2012 | Keren et al. |
| 8,128,689 | B2 | 3/2012 | Weber et al. |
| 8,137,323 | B2 | 3/2012 | Rosenberg et al. |
| 8,152,773 | B2 | 4/2012 | Albrecht et al. |
| 8,182,527 | B2 | 5/2012 | Llanos et al. |
| 8,214,015 | B2 | 7/2012 | Macaulay et al. |
| 8,221,495 | B2 | 7/2012 | Shrivastava et al. |
| 8,226,592 | B2 | 7/2012 | Brenneman et al. |
| D665,500 | S | 8/2012 | Martin et al. |
| 8,282,591 | B2 | 10/2012 | Khan et al. |
| 8,308,682 | B2 | 11/2012 | Kramer et al. |
| 8,357,193 | B2 | 1/2013 | Phan et al. |
| 8,376,979 | B2 | 2/2013 | Kapadia |

(56) References Cited

U.S. PATENT DOCUMENTS

| | | | |
|---|---|---|---|
| 8,382,697 B2 | 2/2013 | Brenneman et al. |
| D679,015 S | 3/2013 | Nakaji |
| 8,409,167 B2 | 4/2013 | Roschak |
| 8,500,697 B2 | 8/2013 | Kurth et al. |
| 8,506,984 B2 | 8/2013 | Cook et al. |
| 8,518,062 B2 | 8/2013 | Cole et al. |
| 8,518,662 B2 | 8/2013 | Ritzen et al. |
| 8,545,552 B2 | 10/2013 | Garrison et al. |
| 8,641,724 B2 | 2/2014 | Brenneman et al. |
| 8,657,790 B2 | 2/2014 | Tal et al. |
| 8,696,611 B2 | 4/2014 | Nitzan et al. |
| D705,427 S | 5/2014 | Jagger et al. |
| 8,768,487 B2 | 7/2014 | Farnan et al. |
| 8,784,860 B2 | 7/2014 | Falotico et al. |
| 8,882,830 B2 | 11/2014 | Cartledge et al. |
| 8,920,449 B2 | 12/2014 | Wilkinson |
| 8,926,545 B2 | 1/2015 | Brenneman et al. |
| 8,932,341 B2 | 1/2015 | Brenneman |
| D723,166 S | 2/2015 | Igaki et al. |
| 8,951,276 B2 | 2/2015 | Kellerman et al. |
| 9,005,155 B2 | 4/2015 | Sugimoto |
| 9,044,588 B2 | 6/2015 | Conn |
| 9,061,115 B2 | 6/2015 | Ward et al. |
| 9,067,050 B2 | 6/2015 | Gallagher et al. |
| 9,108,025 B2 | 8/2015 | Spenser et al. |
| 9,198,756 B2 | 12/2015 | Aklog et al. |
| 9,232,997 B2 | 1/2016 | Sugimoto et al. |
| 9,277,995 B2 | 3/2016 | Celermajer et al. |
| 9,345,485 B2 | 5/2016 | Dakin et al. |
| 9,352,172 B2 | 5/2016 | Benson |
| 9,439,746 B2 | 9/2016 | Bell et al. |
| 9,456,812 B2 | 10/2016 | Finch et al. |
| 9,550,022 B2 | 1/2017 | Brenneman et al. |
| 9,649,480 B2 | 5/2017 | Sugimoto et al. |
| 9,655,666 B2 | 5/2017 | Markowitz et al. |
| 9,681,948 B2 | 6/2017 | Levi et al. |
| 9,693,800 B2 | 7/2017 | Aman et al. |
| 9,775,636 B2 | 10/2017 | Fazio et al. |
| 9,789,294 B2 | 10/2017 | Taft et al. |
| 9,814,483 B2 | 11/2017 | Vardi |
| 9,827,404 B2 | 11/2017 | Nance et al. |
| 9,839,517 B2 | 12/2017 | Centola et al. |
| 9,872,981 B2 | 1/2018 | Sparks et al. |
| 9,980,815 B2 | 5/2018 | Nitzan et al. |
| 10,039,905 B1 | 8/2018 | Taft et al. |
| 10,076,403 B1 | 9/2018 | Eigler et al. |
| 10,130,371 B2 | 11/2018 | Dehdashtian et al. |
| 10,272,230 B2 | 4/2019 | Malek et al. |
| 10,292,690 B2 | 5/2019 | Celermajer et al. |
| 10,327,746 B2 | 6/2019 | Glimsdale et al. |
| 10,413,284 B2 | 9/2019 | McNamara et al. |
| 10,426,482 B2 | 10/2019 | Rafiee et al. |
| 10,426,497 B2 | 10/2019 | Chou et al. |
| 10,433,851 B2 | 10/2019 | Adams et al. |
| 10,456,259 B2 | 10/2019 | Subramanian et al. |
| 10,543,113 B2 | 1/2020 | Vong et al. |
| 10,561,423 B2 | 2/2020 | Sharma |
| 10,565,835 B2 | 2/2020 | Harrington et al. |
| 10,568,751 B2 | 2/2020 | McNamara |
| 10,595,999 B2 | 3/2020 | Vettukattil et al. |
| 10,709,451 B2 | 7/2020 | Gronberg et al. |
| 10,835,394 B2 | 11/2020 | Nae et al. |
| 10,898,698 B1 | 1/2021 | Eigler et al. |
| 10,912,585 B2 | 2/2021 | Kleyman |
| 10,925,731 B2 | 2/2021 | Bishop et al. |
| 10,925,756 B2 | 2/2021 | Perszyk |
| 10,940,296 B2 | 3/2021 | Keren |
| 11,135,054 B2 | 10/2021 | Nitzan et al. |
| 11,135,410 B2 | 10/2021 | Finch et al. |
| 11,234,702 B1 | 2/2022 | Eigler et al. |
| 11,291,807 B2 | 4/2022 | Eigler et al. |
| 11,298,117 B2 | 4/2022 | Hariton et al. |
| 11,304,698 B2 | 4/2022 | Sharma |
| 11,395,644 B2 | 7/2022 | Alanbaei |
| 11,420,034 B2 | 8/2022 | Solomon et al. |
| 2001/0000041 A1 | 3/2001 | Selmon et al. |
| 2001/0025643 A1 | 10/2001 | Foley |
| 2001/0035183 A1 | 11/2001 | Sexton et al. |
| 2001/0045698 A1 | 11/2001 | Lo |
| 2002/0013616 A1 | 1/2002 | Carter et al. |
| 2002/0029079 A1 | 3/2002 | Kim et al. |
| 2002/0062146 A1 | 5/2002 | Makower et al. |
| 2002/0128546 A1 | 9/2002 | Silver |
| 2002/0138009 A1 | 9/2002 | Brockway et al. |
| 2002/0169466 A1 | 11/2002 | Peterson et al. |
| 2002/0193751 A1 | 12/2002 | Theeuwes et al. |
| 2002/0198501 A1 | 12/2002 | Kumar et al. |
| 2003/0017150 A1 | 1/2003 | Torphy |
| 2003/0060876 A1 | 3/2003 | Loshakove et al. |
| 2003/0065345 A1 | 4/2003 | Weadock |
| 2003/0181928 A1 | 9/2003 | Vidlund et al. |
| 2003/0225425 A1 | 12/2003 | Kupiecki et al. |
| 2004/0064081 A1 | 4/2004 | Stanish |
| 2004/0082738 A1 | 4/2004 | Dolle et al. |
| 2004/0087997 A1 | 5/2004 | Brenneman |
| 2004/0092879 A1 | 5/2004 | Kraus et al. |
| 2004/0098105 A1 | 5/2004 | Stinson et al. |
| 2004/0158143 A1 | 8/2004 | Flaherty et al. |
| 2004/0215168 A1 | 10/2004 | Verrier et al. |
| 2004/0215220 A1 | 10/2004 | Dolan et al. |
| 2004/0215323 A1 | 10/2004 | Stiger |
| 2004/0230156 A1 | 11/2004 | Schreck et al. |
| 2004/0260318 A1 | 12/2004 | Hunter et al. |
| 2005/0021085 A1 | 1/2005 | Abrams et al. |
| 2005/0033239 A1 | 2/2005 | Argentine |
| 2005/0038501 A1 | 2/2005 | Moore et al. |
| 2005/0043708 A1 | 2/2005 | Gleeson et al. |
| 2005/0049675 A1 | 3/2005 | Wallace |
| 2005/0060041 A1 | 3/2005 | Phan et al. |
| 2005/0065469 A1 | 3/2005 | Tal |
| 2005/0075655 A1 | 4/2005 | Bumbalough et al. |
| 2005/0075656 A1 | 4/2005 | Beaupre |
| 2005/0082226 A1 | 4/2005 | Bene et al. |
| 2005/0107723 A1 | 5/2005 | Wehman et al. |
| 2005/0149096 A1 | 7/2005 | Hilal et al. |
| 2005/0165344 A1 | 7/2005 | Dobak |
| 2005/0228402 A1 | 10/2005 | Hofmann |
| 2005/0249770 A1 | 11/2005 | Hunter |
| 2005/0249776 A1 | 11/2005 | Chen et al. |
| 2005/0267490 A1 | 12/2005 | Secrest et al. |
| 2005/0272806 A1 | 12/2005 | Falotico et al. |
| 2005/0277965 A1 | 12/2005 | Brenneman et al. |
| 2006/0020324 A1 | 1/2006 | Schmid et al. |
| 2006/0024359 A1 | 2/2006 | Walker et al. |
| 2006/0034466 A1 | 2/2006 | Form et al. |
| 2006/0041270 A1 | 2/2006 | Lenker et al. |
| 2006/0074398 A1 | 4/2006 | Whiting et al. |
| 2006/0111704 A1 | 5/2006 | Brenneman et al. |
| 2006/0130591 A1 | 6/2006 | Perkins |
| 2006/0130767 A1 | 6/2006 | Herchen |
| 2006/0182536 A1 | 8/2006 | Rice et al. |
| 2006/0198869 A1 | 9/2006 | Furst et al. |
| 2006/0241342 A1 | 10/2006 | Macaulay et al. |
| 2006/0264801 A1 | 11/2006 | Bolling et al. |
| 2006/0265042 A1 | 11/2006 | Catanese et al. |
| 2006/0271196 A1 | 11/2006 | Saal et al. |
| 2006/0293701 A1 | 12/2006 | Ainsworth et al. |
| 2007/0021730 A1 | 1/2007 | Flaherty et al. |
| 2007/0083258 A1 | 4/2007 | Falotico et al. |
| 2007/0173787 A1 | 7/2007 | Huang et al. |
| 2007/0179426 A1 | 8/2007 | Selden |
| 2007/0213750 A1 | 9/2007 | Weadock |
| 2008/0021485 A1 | 1/2008 | Catanese et al. |
| 2008/0027532 A1 | 1/2008 | Boylan et al. |
| 2008/0051883 A1 | 2/2008 | Llanos et al. |
| 2008/0065009 A1 | 3/2008 | Ben-Muvhar |
| 2008/0071178 A1 | 3/2008 | Greenland et al. |
| 2008/0091264 A1 | 4/2008 | Machold et al. |
| 2008/0109069 A1 | 5/2008 | Coleman et al. |
| 2008/0161904 A1 | 7/2008 | Heuser et al. |
| 2008/0167595 A1 | 7/2008 | Porter et al. |
| 2008/0234842 A1 | 9/2008 | Zhang |
| 2008/0306359 A1 | 12/2008 | Zdeblick et al. |
| 2009/0005656 A1 | 1/2009 | Najafi et al. |

(56) References Cited

U.S. PATENT DOCUMENTS

| | | |
|---|---|---|
| 2009/0105654 A1 | 4/2009 | Kurth et al. |
| 2009/0125097 A1 | 5/2009 | Bruszewski et al. |
| 2009/0143713 A1 | 6/2009 | Van Dam et al. |
| 2009/0149947 A1 | 6/2009 | Frohwitter |
| 2009/0187116 A1 | 7/2009 | Noishiki et al. |
| 2009/0234293 A1 | 9/2009 | Albrecht et al. |
| 2009/0281379 A1 | 11/2009 | Binmoeller et al. |
| 2010/0016797 A1 | 1/2010 | Rockrohr |
| 2010/0030321 A1 | 2/2010 | Mach |
| 2010/0106171 A1 | 4/2010 | Arepally et al. |
| 2010/0198041 A1 | 8/2010 | Christian et al. |
| 2010/0217382 A1 | 8/2010 | Chau et al. |
| 2010/0298930 A1 | 11/2010 | Orlov |
| 2011/0096036 A1 | 4/2011 | McIntosh et al. |
| 2011/0106118 A1 | 5/2011 | Son et al. |
| 2011/0251482 A1 | 10/2011 | Kellerman et al. |
| 2011/0306916 A1 | 12/2011 | Nitzan et al. |
| 2012/0029598 A1 | 2/2012 | Zhao |
| 2012/0041544 A1 | 2/2012 | Wolf |
| 2012/0053686 A1 | 3/2012 | McNamara et al. |
| 2012/0108986 A1 | 5/2012 | Beasley et al. |
| 2012/0143141 A1 | 6/2012 | Verkaik et al. |
| 2012/0265229 A1 | 10/2012 | Rottenberg et al. |
| 2012/0265296 A1 | 10/2012 | McNamara et al. |
| 2013/0006282 A1 | 1/2013 | Wilkinson |
| 2013/0022214 A1 | 1/2013 | Dickins et al. |
| 2013/0030521 A1 | 1/2013 | Nitzan et al. |
| 2013/0178784 A1 | 7/2013 | McNamara et al. |
| 2013/0218054 A1 | 8/2013 | Sverdlik et al. |
| 2013/0225997 A1 | 8/2013 | Dillard et al. |
| 2013/0253342 A1 | 9/2013 | Griswold et al. |
| 2013/0281988 A1 | 10/2013 | Magnin et al. |
| 2014/0094836 A1 | 4/2014 | Feng et al. |
| 2014/0183828 A1 | 7/2014 | Xu et al. |
| 2014/0203939 A1 | 7/2014 | Harrington et al. |
| 2014/0222040 A1 | 8/2014 | Park et al. |
| 2014/0276395 A1 | 9/2014 | Wilson et al. |
| 2014/0277054 A1 | 9/2014 | McNamara et al. |
| 2014/0278442 A1 | 9/2014 | Hong et al. |
| 2014/0350523 A1 | 11/2014 | Dehdashtian et al. |
| 2015/0119796 A1 | 4/2015 | Finch |
| 2015/0148731 A1 | 5/2015 | Mcnamara et al. |
| 2015/0151101 A1 | 6/2015 | Bonnette et al. |
| 2015/0238729 A1 | 8/2015 | Jenson et al. |
| 2015/0320330 A1* | 11/2015 | Sparks ................... A61N 1/057 |
| | | 600/375 |
| 2016/0022293 A1 | 1/2016 | Dubrul et al. |
| 2016/0022970 A1 | 1/2016 | Forcucci et al. |
| 2016/0045165 A1 | 2/2016 | Braido et al. |
| 2016/0058452 A1 | 3/2016 | Brenneman et al. |
| 2016/0120550 A1 | 5/2016 | McNamara et al. |
| 2016/0151615 A1 | 6/2016 | Overtoom |
| 2016/0220357 A1 | 8/2016 | Anand et al. |
| 2016/0270810 A1 | 9/2016 | Vardi et al. |
| 2016/0296317 A1 | 10/2016 | Timmermans et al. |
| 2016/0323977 A1 | 11/2016 | Sun et al. |
| 2016/0331468 A1 | 11/2016 | Lee et al. |
| 2016/0338823 A1 | 11/2016 | Akingba |
| 2017/0020540 A1 | 1/2017 | Chou et al. |
| 2017/0090865 A1 | 3/2017 | Armstrong-Muntner et al. |
| 2017/0105839 A1 | 4/2017 | Subramanian et al. |
| 2017/0106176 A1 | 4/2017 | Taft et al. |
| 2017/0113026 A1 | 4/2017 | Finch |
| 2017/0128705 A1 | 5/2017 | Forcucci et al. |
| 2017/0196565 A1 | 7/2017 | Tuseth et al. |
| 2017/0258585 A1 | 9/2017 | Marquez et al. |
| 2017/0303959 A1 | 10/2017 | Feng et al. |
| 2017/0319823 A1 | 11/2017 | Yacoby et al. |
| 2017/0340460 A1 | 11/2017 | Rosen et al. |
| 2018/0035971 A1 | 2/2018 | Brenner et al. |
| 2018/0140444 A1 | 5/2018 | Neuss et al. |
| 2018/0177516 A1 | 6/2018 | Vardi et al. |
| 2018/0185153 A1 | 7/2018 | Bishop et al. |
| 2018/0207412 A1 | 7/2018 | Malek et al. |
| 2018/0214269 A1 | 8/2018 | Wilson et al. |
| 2018/0243071 A1 | 8/2018 | Eigler et al. |
| 2018/0256865 A1 | 9/2018 | Finch et al. |
| 2019/0008628 A1 | 1/2019 | Eigler et al. |
| 2019/0083228 A1 | 3/2019 | Dickinson et al. |
| 2019/0134350 A1* | 5/2019 | Crisco ............... A61M 25/0194 |
| 2019/0269392 A1 | 9/2019 | Celermajer et al. |
| 2019/0298909 A1 | 10/2019 | Cully et al. |
| 2019/0336339 A1 | 11/2019 | Reo et al. |
| 2019/0351210 A1 | 11/2019 | Solomon et al. |
| 2020/0054867 A1 | 2/2020 | Schwartz et al. |
| 2020/0085600 A1 | 3/2020 | Schwartz et al. |
| 2020/0101270 A1 | 4/2020 | Sutherland |
| 2020/0170662 A1 | 6/2020 | Vardi et al. |
| 2020/0187945 A1 | 6/2020 | Rowe et al. |
| 2020/0230362 A1 | 7/2020 | Basude |
| 2020/0254228 A1 | 8/2020 | Taft et al. |
| 2020/0261704 A1 | 8/2020 | Wang et al. |
| 2020/0289196 A1 | 9/2020 | Arevalos et al. |
| 2020/0315599 A1 | 10/2020 | Nae et al. |
| 2020/0368505 A1 | 11/2020 | Nae et al. |
| 2020/0391016 A1 | 12/2020 | Passman et al. |
| 2021/0007790 A1 | 1/2021 | Takahashi et al. |
| 2021/0007791 A1 | 1/2021 | Takahashi et al. |
| 2021/0007800 A1 | 1/2021 | Takahashi et al. |
| 2021/0022855 A1 | 1/2021 | Tegels et al. |
| 2021/0045691 A1 | 2/2021 | Zou et al. |
| 2021/0052877 A1 | 2/2021 | Muldoon et al. |
| 2021/0059650 A1 | 3/2021 | Eidenschink et al. |
| 2021/0077186 A1 | 3/2021 | Pate et al. |
| 2021/0085935 A1 | 3/2021 | Fahey et al. |
| 2021/0092522 A1 | 3/2021 | Draper et al. |
| 2021/0113824 A1 | 4/2021 | Chng et al. |
| 2021/0121179 A1 | 4/2021 | Ben-David et al. |
| 2021/0137635 A1 | 5/2021 | Gomez et al. |
| 2021/0153776 A1 | 5/2021 | Minar et al. |
| 2021/0161637 A1 | 6/2021 | Eigler et al. |
| 2021/0177508 A1 | 6/2021 | Kellerman |
| 2021/0213269 A1 | 7/2021 | Venskytis et al. |
| 2021/0236138 A1 | 8/2021 | Perszyk et al. |
| 2021/0259671 A1 | 8/2021 | DiCicco et al. |
| 2021/0290214 A1 | 9/2021 | Cole et al. |
| 2021/0361238 A1 | 11/2021 | Bak-Boychuk et al. |
| 2021/0369321 A1 | 12/2021 | Yang et al. |
| 2021/0401494 A1 | 12/2021 | Passman et al. |
| 2022/0001154 A1 | 1/2022 | Rowe et al. |
| 2022/0008014 A1 | 1/2022 | Rowe et al. |
| 2022/0031327 A1 | 2/2022 | Manash et al. |
| 2022/0039667 A1 | 2/2022 | Schmitt et al. |
| 2022/0039671 A1 | 2/2022 | Fahey |
| 2022/0039833 A1 | 2/2022 | Thai et al. |
| 2022/0088355 A1 | 3/2022 | Rabito et al. |
| 2022/0096087 A1 | 3/2022 | Valdez |
| 2022/0110679 A1 | 4/2022 | Wang et al. |
| 2022/0142652 A1 | 5/2022 | Alexander et al. |
| 2022/0151784 A1 | 5/2022 | Eigler et al. |
| 2022/0168015 A1 | 6/2022 | Murray et al. |
| 2022/0184356 A1 | 6/2022 | Nae et al. |
| 2022/0202443 A1 | 6/2022 | Thai et al. |
| 2022/0203077 A1 | 6/2022 | Folan |
| 2022/0203078 A1 | 6/2022 | May |
| 2022/0211380 A1 | 7/2022 | Pate |
| 2022/0218352 A1 | 7/2022 | O'Halloran et al. |
| 2022/0218964 A1 | 7/2022 | Fahey et al. |
| 2022/0241564 A1 | 8/2022 | Shang et al. |
| 2022/0241565 A1 | 8/2022 | Nae et al. |
| 2022/0249285 A1 | 8/2022 | Chang et al. |
| 2022/0257904 A1 | 8/2022 | Passman et al. |
| 2022/0273279 A1 | 9/2022 | Valdez et al. |
| 2022/0280160 A1 | 9/2022 | Sharma |
| 2022/0280760 A1 | 9/2022 | Thai et al. |
| 2022/0296865 A1 | 9/2022 | Rafiee et al. |
| 2022/0313234 A1 | 10/2022 | Mcnamara et al. |
| 2022/0323012 A1 | 10/2022 | Pool et al. |
| 2022/0323196 A1 | 10/2022 | Rafiee et al. |
| 2022/0346936 A1 | 11/2022 | Scutti et al. |
| 2022/0347446 A1 | 11/2022 | Fahey et al. |
| 2022/0370120 A1 | 11/2022 | Yang et al. |
| 2022/0379100 A1 | 12/2022 | Gutierrez et al. |
| 2022/0387009 A1 | 12/2022 | Bukhdruker et al. |

(56) References Cited

U.S. PATENT DOCUMENTS

| | | |
|---|---|---|
| 2023/0099410 A1 | 3/2023 | Primeaux |
| 2023/0165672 A1 | 6/2023 | Fahey et al. |
| 2023/0181214 A1 | 6/2023 | Vardi et al. |
| 2023/0191093 A1 | 6/2023 | Nae et al. |
| 2023/0233255 A1 | 7/2023 | Takahashi |
| 2023/0263949 A1 | 8/2023 | Passman et al. |
| 2023/0285133 A1 | 9/2023 | Eigler et al. |
| 2023/0330398 A1 | 10/2023 | Nae et al. |
| 2023/0404659 A1 | 12/2023 | Akerele-Ale et al. |
| 2024/0000404 A1 | 1/2024 | Robertson et al. |

FOREIGN PATENT DOCUMENTS

| | | |
|---|---|---|
| CN | 113397762 A | 9/2021 |
| KR | 20200145957 A | 12/2020 |
| WO | WO-2005006963 A2 | 1/2005 |
| WO | WO-2014150106 A1 | 9/2014 |
| WO | WO-2015052235 A1 | 4/2015 |
| WO | WO-2019035993 A1 | 2/2019 |
| WO | 2020215090 A1 | 10/2020 |
| WO | WO-2020232384 A1 | 11/2020 |
| WO | 2021091566 A1 | 5/2021 |
| WO | 2022031317 A1 | 2/2022 |
| WO | 2022060630 A1 | 3/2022 |
| WO | WO-2022071179 A1 | 4/2022 |
| WO | 2022133070 A1 | 6/2022 |
| WO | 2022169865 A1 | 8/2022 |
| WO | 2022177737 A1 | 8/2022 |
| WO | 2022197454 A1 | 9/2022 |
| WO | 2022197455 A1 | 9/2022 |
| WO | 2022232133 A1 | 11/2022 |
| WO | 2022246158 A1 | 11/2022 |
| WO | 2022246166 A1 | 11/2022 |
| WO | 2022271473 A1 | 12/2022 |
| WO | 2023022883 A1 | 2/2023 |
| WO | 2023027926 A1 | 3/2023 |
| WO | 2023079498 A1 | 5/2023 |
| WO | 2023081127 A1 | 5/2023 |
| WO | 2023081129 A1 | 5/2023 |
| WO | 2023154235 A1 | 8/2023 |
| WO | 2023154308 A1 | 8/2023 |
| WO | 2023172435 A1 | 9/2023 |
| WO | 2023172436 A1 | 9/2023 |
| WO | 2023196243 A1 | 10/2023 |
| WO | 2023239784 A1 | 12/2023 |
| WO | 2023239785 A1 | 12/2023 |
| WO | 2023239788 A2 | 12/2023 |
| WO | WO-2024076579 A1 | 4/2024 |

OTHER PUBLICATIONS

Kong, et al.—Creation of an Intra-atrial Communication With a New Amplatzer Shunt Prosthesis, Catheterization and Cardiovascular Interventions 56:267-271 (2002).

P.K. Kong, et al., Title: Unroofed Coronary Sinus and Persistent Left Superior Vena Cava, The European Society of Cardiology, 2006, p. 398401.

Ruebben et al., "Arteriovenous fistulas induced by femoral arterial catheterization: percuntaneous treatment," Radiology, 209:729, 1998.

Vandhana Scheller, et al., Title: Coronary Sinus to Left Atrial Communication, Case Report in Medicine, Ohio Heart and Vascular Center, vol. 2009, Article ID 790715, p. 13.

Bechtold C., et al., "Method for Fabricating Miniaturized NiTi Self-Expandable Thin Film Devices with Increased Radiopacity", Shape Memory and Superelasticity, 2016, vol. 2, pp. 391-398.

Chao-Chi Y., et al., "Fabrication of a Flexible Wireless Pressure Sensor for Intravascular Blood Pressure Monitoring," Microelectronic Engineering Elsevier Publishers Bv, Amsterdam, NL, Apr. 11, 2019, vol. 213, pp. 55-61, ISSN 0167-9317, XP085679189, Retrieved from URL: http://dx.doi.Org/10.1016/j.mee.2019.04.009.

* cited by examiner

SECURING A GUIDEWIRE DELIVERY CATHETER IN THE CORONARY SINUS USING A MECHANICALLY RELEASING ARM

CROSS-REFERENCE TO RELATED APPLICATION

This application is a continuation of International Patent Application No. PCT/US2022/030195, filed May 20, 2022 and entitled SECURING A GUIDEWIRE DELIVERY CATHETER IN THE CORONARY SINUS USING A MECHANICALLY RELEASING ARM, which claims the benefit of priority of U.S. Prov. App. No. 63/191,419, filed May 21, 2021 and entitled SECURING A GUIDEWIRE DELIVERY CATHETER IN THE CORONARY SINUS USING A MECHANICALLY RELEASING ARM, the complete disclosures of which are hereby incorporated by reference in their entireties for all purposes.

BACKGROUND

Field

The present invention relates generally to the field of delivery devices, such as catheters, for medical procedures involving the coronary sinus.

Description of Related Art

Heart failure is a common and potentially lethal condition affecting humans, with sub-optimal clinical outcomes often resulting in morbidity and/or mortality, despite maximal medical treatment. In particular, "diastolic heart failure" refers to the clinical syndrome of heart failure occurring in the context of preserved left ventricular systolic function (ejection fraction) and in the absence of major valvular disease. This condition is characterized by a stiff left ventricle with decreased compliance and impaired relaxation, which leads to increased end-diastolic pressure.

Symptoms of diastolic heart failure are due, at least in large part, to an elevation in pressure in the left atrium. Elevated left atrial pressure (LAP) is present in several abnormal heart conditions, including heart failure (HF). In addition to diastolic heart failure, a number of other medical conditions, including systolic dysfunction of the left ventricle and valve disease, can lead to elevated pressures in the left atrium. Both heart failure with preserved ejection fraction (HFpEF) and heart failure with reduced ejection fraction (HFrEF) can exhibit elevated LAP.

It may be beneficial to reduce elevated pressure in the left atrium. One way to do this is to shunt blood from the left atrium to the coronary sinus. By creating an opening between the left atrium and the coronary sinus, blood will flow from the higher pressure left atrium to the lower pressure coronary sinus. Examples of methods to shunt blood from the left atrium to the coronary sinus are disclosed in U.S. Pat. No. 9,789,294 entitled "Expandable Cardiac Shunt," the entire contents of which is incorporated by reference herein.

Using catheter-based instruments, the surgeon creates a puncture hole between the left atrium and the coronary sinus and places an expandable shunt within the puncture hole. To do this, one or more catheters are used to create the puncture hole, to deliver the expandable shunt along a guidewire, and to deploy the expandable shunt in the puncture hole. Once expanded, the shunt defines a blood flow passage that allows blood to flow from the left atrium to the coronary sinus when the LAP is elevated.

SUMMARY

For purposes of summarizing the disclosure, certain aspects, advantages and novel features have been described herein. It is to be understood that not necessarily all such advantages may be achieved in accordance with any particular example. Thus, the disclosed examples may be carried out in a manner that achieves or optimizes one advantage or group of advantages as taught herein without necessarily achieving other advantages as may be taught or suggested herein.

Some implementations of the present disclosure relate to a guidewire delivery catheter used to implant a shunt between the coronary sinus and the left atrium. The catheter includes a needle housed within the catheter in a delivery configuration, the needle configured to extend out of the catheter to puncture a vessel wall in a deployment configuration. The catheter includes a needle port through which the needle extends out of the catheter to transition from the delivery configuration to the deployment configuration. The catheter includes a securing mechanism housed within the catheter in a delivery configuration, the securing mechanism comprising a compliant wire configured to be advanced out of the catheter in a deployment configuration so that a distal portion of the wire comes into contact with the vessel wall to provide wall apposition for the needle to puncture the vessel wall. The catheter includes a wire port through which the wire of the securing mechanism extends out of the catheter to transition from the delivery configuration to the deployment configuration.

In some examples, a distal portion of the wire of the securing mechanism is configured to coil upon exiting the wire port.

In some examples, the catheter further includes a second wire port, wherein the securing mechanism further comprises a second wire configured to exit the catheter at the second wire port. In further examples, each of the wires of the securing mechanism is configured to curve away from the catheter in the deployment configuration. In further examples, an azimuth angle between the needle port and each of the two wire ports is at least 90 degrees and less than 180 degrees. In further examples, an azimuth angle between the needle port and each of the two wire ports is at least 120 degrees. In further examples, an azimuth angle ($\theta1$) between the two wire ports is less than or equal to 120 degrees.

In some examples, the securing mechanism further includes a curved endcap at a distal end of the wire. In further examples, the curved endcap is configured to contact the vessel wall in the deployment configuration. In further examples, the curved endcap is configured to cover the wire port in the delivery configuration. In further examples, the curved endcap is configured to follow a contour of the vessel wall.

In some examples, the wire is configured to run along a length of the catheter such that the wire is configured to be advanced by manipulating a component of the securing mechanism from outside of an operative site.

In some examples, the wire comprises a shape memory metal. In further examples, the wire is shape set to curve away from the catheter. In further examples, the wire is shape set to coil outside of the catheter. In further examples, the wire is shape set to exit the catheter at an exit angle. In further examples, a distal end of the catheter is coated with a material to reduce a likelihood of damaging the vessel wall.

In some examples, the wire is configured to be withdrawn to transition from the deployment configuration back to the delivery configuration. In some examples, the wire port is positioned opposite the needle port so that the wire exits the catheter on an opposite side from where the needle exits the catheter. In some examples, wire port is positioned more distally along the catheter relative to the needle port.

BRIEF DESCRIPTION OF THE DRAWINGS

Various examples are depicted in the accompanying drawings for illustrative purposes and should in no way be interpreted as limiting the scope of the disclosed subject matter. In addition, various features of different disclosed examples can be combined to form additional examples, which are part of this disclosure. Throughout the drawings, reference numbers may be reused to indicate correspondence between reference elements. However, it should be understood that the use of similar reference numbers in connection with multiple drawings does not necessarily imply similarity between respective examples associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some examples or configurations.

DETAILED DESCRIPTION

Figures 1, 2:
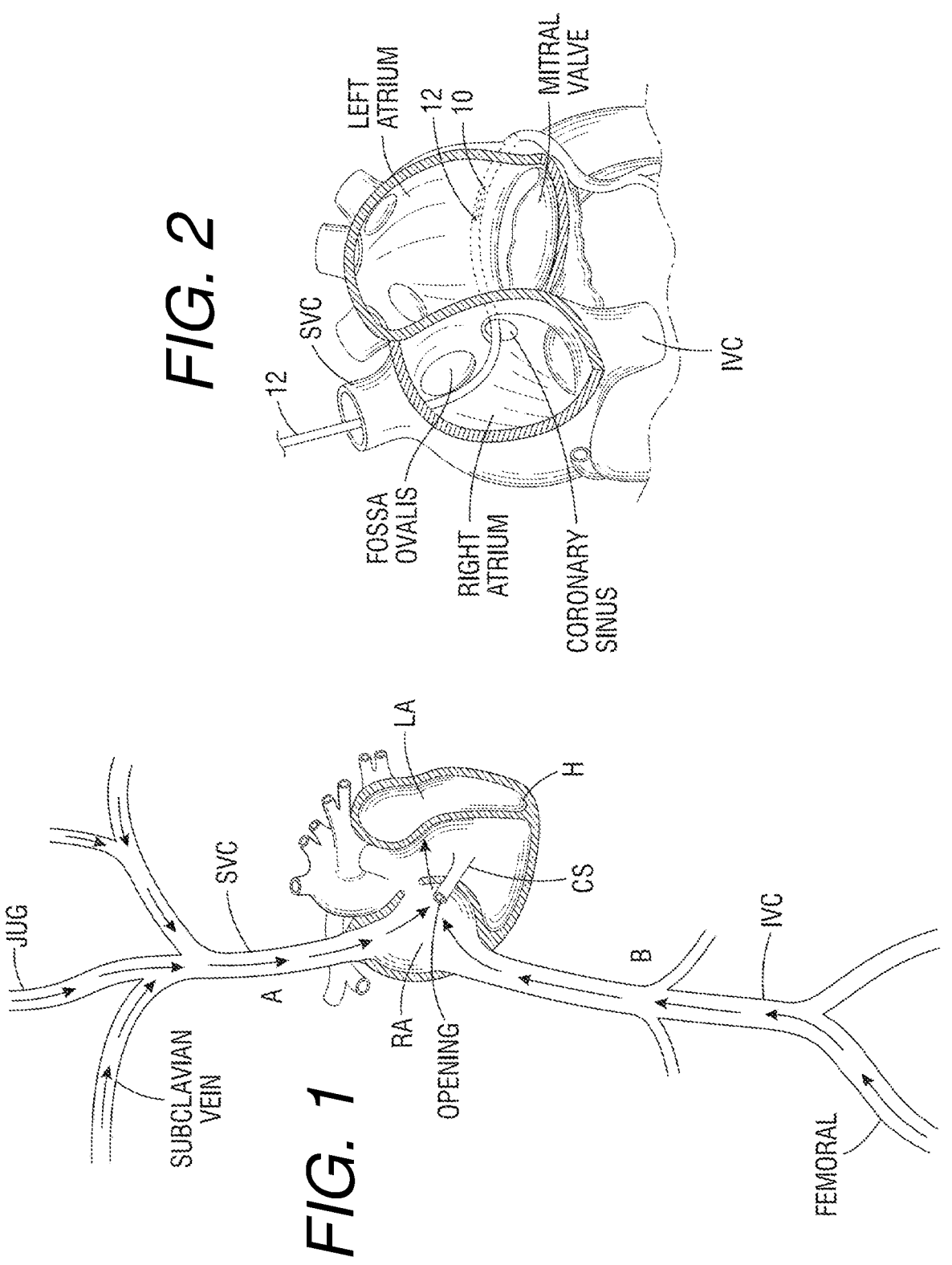
FIG. 1 illustrates several access pathways for maneuvering guidewires and catheters in and around the heart to deploy shunts.
FIG. 2 depicts one approach method for deploying an expandable shunt, wherein a guidewire is introduced through the subclavian or jugular vein, through the superior vena cava and into the coronary sinus.

The headings provided herein are for convenience only and do not necessarily affect the scope or meaning of the claimed subject matter.

Overview

Symptoms of diastolic heart failure arise from elevated pressure in the left atrium, or elevated left atrial pressure (LAP). Other heart conditions may manifest elevated LAP as well. To reduce the pressure in the left atrium, a pathway can be created between the left atrium and the coronary sinus. This allows blood to flow from the higher pressure left atrium to the lower pressure coronary sinus. The pathway can be created by puncturing a hole between the left atrium and the coronary sinus. Once the hole has been created, a shunt can be placed in the hole to keep it open.

For example, catheter-based instruments can be used to create the hole and to deliver and deploy a shunt within the puncture hole. The catheter can be referred to as a guidewire delivery catheter (GDC) and can be used to puncture through the coronary sinus into the left atrium and to place a guidewire in the left atrium. To puncture through the tissue, the catheter has wall apposition to get the needle directly against the coronary sinus-left atrium wall. Prior GDCs used an "anchor balloon" (a saline-inflated balloon) to anchor the catheter when creating the puncture hole. The anchor balloon solution has the potential to burst or to slip out of position, which may harm the patient.

Accordingly, described herein are materials and mechanisms for securing the GDC in place to enable the GDC to puncture the wall from the coronary sinus to the left atrium. These materials and mechanisms serve as an alternative to the anchor balloon.

The term "catheter" is used herein according to its broad and ordinary meaning and may include any tube, sheath, steerable sheath, steerable catheters, and/or any other type of elongate tubular delivery device comprising an inner lumen configured to slidably receive instrumentation, such as for positioning within an atrium or coronary sinus, including for example delivery catheters and/or cannulas. In some cases, a securing mechanism may be composed of a shape-memory alloy (e.g., Nitinol) and/or may have a pre-defined shape and/or structure. The securing mechanism may be configured to be shaped and/or compressed to fit into and/or around a catheter. In some cases, a securing mechanism may have an elongated shape in a delivery configuration to extend at least partially along the catheter and to change shape in a deployed configuration to provide wall apposition.

Some examples described herein provide methods and/or systems for securing a guidewire delivery catheter, or other similar delivery device, to provide wall apposition for puncturing a vessel wall. While some examples may be directed to securing a catheter within the coronary sinus to puncture the wall between the coronary sinus and the left atrium, the devices described herein may be applicable to other areas of the body. For example, some devices described herein may advantageously be configured for securing catheters to provide wall apposition for puncturing vessels in vessels other than the coronary sinus.

The following includes a general description of a method for delivering a guidewire delivery catheter to a targeted location in the coronary sinus. It is to be understood that the disclosed securing mechanisms can be used in conjunction with such a guidewire delivery catheter in this or similar methods to provide wall apposition for puncturing the coronary sinus. FIG. 1 illustrates several access pathways for maneuvering guidewires and catheters in and around the heart to deploy shunts. For instance, access may be from above via either the subclavian or jugular veins into the superior vena cava (SVC), right atrium (RA) and from there into the coronary sinus (CS). Alternatively, the access path may start in the femoral vein and through the inferior vena cava (IVC) into the heart. Other access routes may also be used, and each typically utilizes a percutaneous incision through which the guidewire and catheter are inserted into the vasculature, normally through a sealed introducer, and from there the physician controls the distal ends of the devices from outside the body.

FIG. 2 depicts an example method for deploying an expandable shunt, wherein a guidewire 10 is introduced through the subclavian or jugular vein, through the superior vena cava and into the coronary sinus. Once the guidewire provides a path, an introducer sheath (not shown) may be routed along the guidewire and into the patient's vasculature, typically with the use of a dilator. FIG. 2 shows a deployment catheter 12 extending from the superior vena cava to the coronary sinus of the heart, the deployment catheter 12 having been passed through the introducer sheath which provides a hemostatic valve to prevent blood loss.

In some examples, the deployment catheter 12 may be about 30 cm long, and the guidewire 10 may be somewhat longer for ease of use. In certain examples, the deployment catheter 12 may function to form and to prepare an opening in the wall of the left atrium, and a separate placement or delivery catheter may be used for delivery of an expandable shunt. In various examples, the deployment catheter may be used for both puncture preparation and shunt placement. In the present application, the terms "deployment catheter" or "delivery catheter" are used to represent a catheter or introducer with one or both of these functions.

Since the coronary sinus is largely contiguous around the left atrium, there are a variety of possible acceptable placements for a stent. The site selected for placement of the stent may be made in an area where the tissue of the particular patient is less thick or less dense, as determined beforehand by non-invasive diagnostic means, such as a CT scan or radiographic technique, such as fluoroscopy or intravascular coronary echo (IVUS).

Figures 3A, 3B:
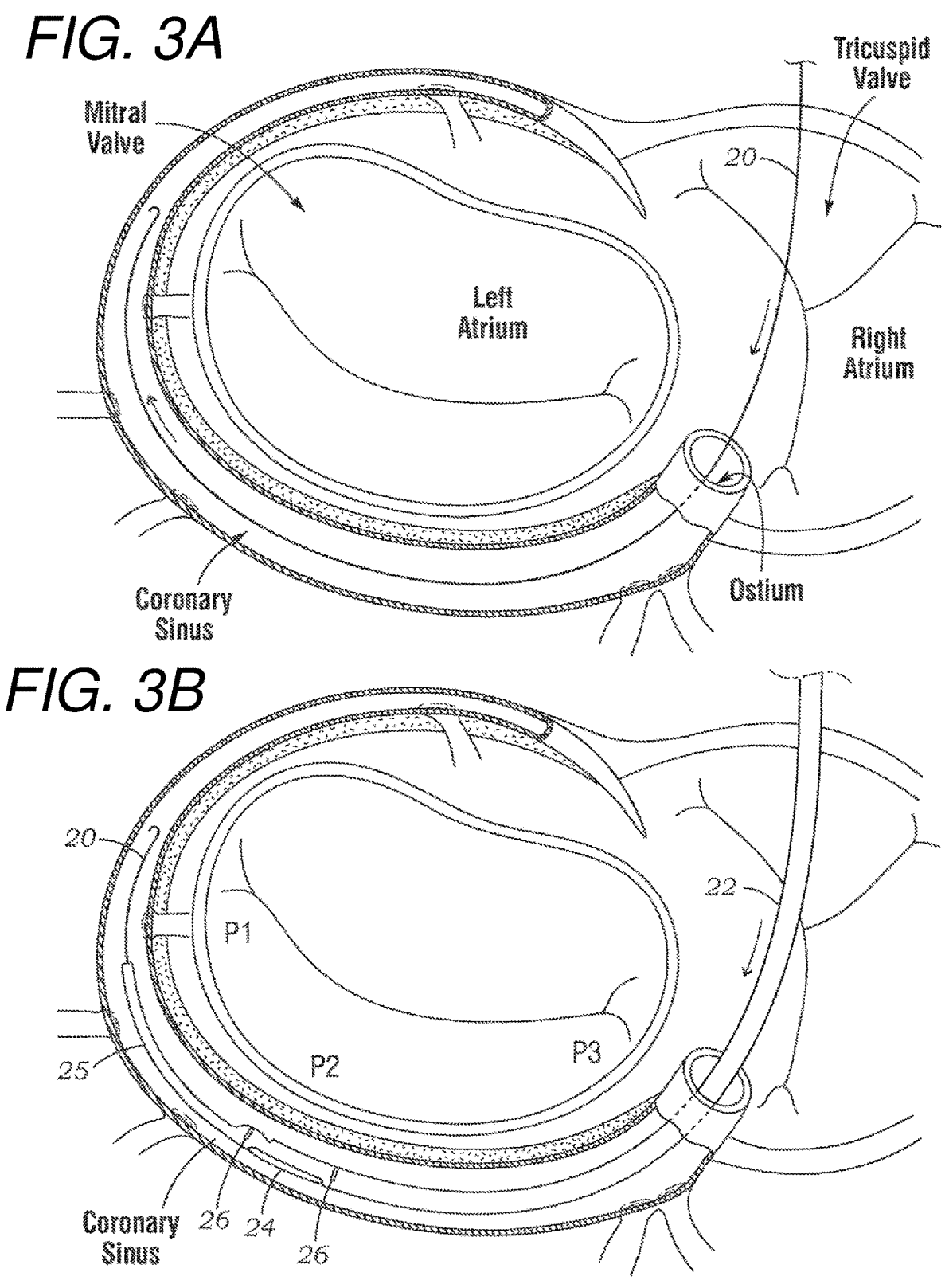
FIGS. 3A, 3B, 3C, and 3D are schematic views of steps in making a puncture hole through a wall of the coronary sinus, as seen looking down on a section of the heart with the posterior aspect down.

FIGS. 3A-3D are schematic views of steps in making a puncture hole through a wall of the coronary sinus, as seen looking down on a section of the heart with the posterior aspect down. Initially, FIG. 3A shows a guidewire 20 being advanced from the right atrium into the coronary sinus through its ostium or opening. A puncture catheter 22 is then advanced over the guidewire 20, as seen in FIG. 3B. The puncture catheter 22 is introduced into the body through a proximal end of an introducer sheath (not shown). As is customary, an introducer sheath provides access to the particular vascular pathway (e.g., jugular or subclavian vein) and may have a hemostatic valve therein. While holding the introducer sheath at a fixed location, the surgeon manipulates the puncture catheter 22 to the implant site.

In certain implementations, a distal end of the puncture catheter 22 has a slight curvature, with a radially inner and a radially outer side, to conform to the curvature of the coronary sinus. A securing mechanism 24 is exposed along the radially outer side of the catheter 22 adjacent an extreme distal segment 25 that may be thinner than or tapered narrower from the proximal extent of the catheter. Radiopaque markers 26 on the catheter 22 help the surgeon determine the precise advancement distance for desired placement of the securing mechanism 24 within the coronary sinus. In some instances, the radiopaque markers 26 are C-shape bands that flank the proximal and distal ends of the securing mechanism 24.

Figure 3C:
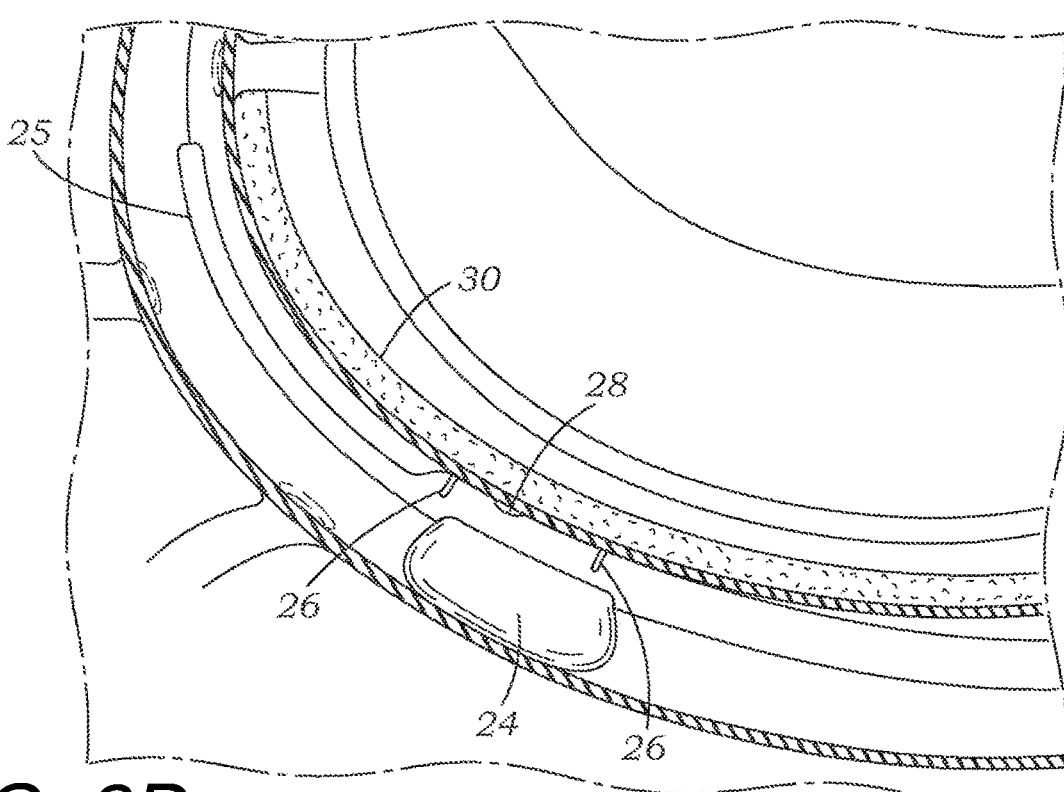

FIG. 3C shows outward deployment of the securing mechanism 24, which is to be considered a generic structure that is replaced by any of the securing mechanisms disclosed herein and described with reference to FIGS. 4A-6C. Deployment of the securing mechanism 24 presses the radially inner curve of the catheter against the luminal wall of the coronary sinus to provide wall apposition. Again, the securing mechanism 24 is located adjacent the distal segment 25 of the puncture catheter 22. In some examples, the securing mechanism 24 extends opposite a needle port 28 formed in the radially inner side wall of the catheter. Consequently, the needle port 28 abuts the luminal wall and faces toward a tissue wall 30 between the coronary sinus and the left atrium. Preferably, guided by visualizing the radiopaque markers 26, the surgeon advances the catheter 22 so that the needle port 28 is located within about 2-4 cm into the coronary ostia. This places the subsequent puncture approximately above the "P2" portion of the posterior leaflet of the mitral valve (when looking at the inflow side of the valve the posterior leaflet has P1-P2-P3 cusps in a CCW direction, as seen in FIG. 3B). The securing mechanism 24 may be centered diametrically across the catheter 22 from the needle port 28, or as shown may be slightly offset in a proximal direction from the needle port 28 to improve leverage.

Figure 3D:
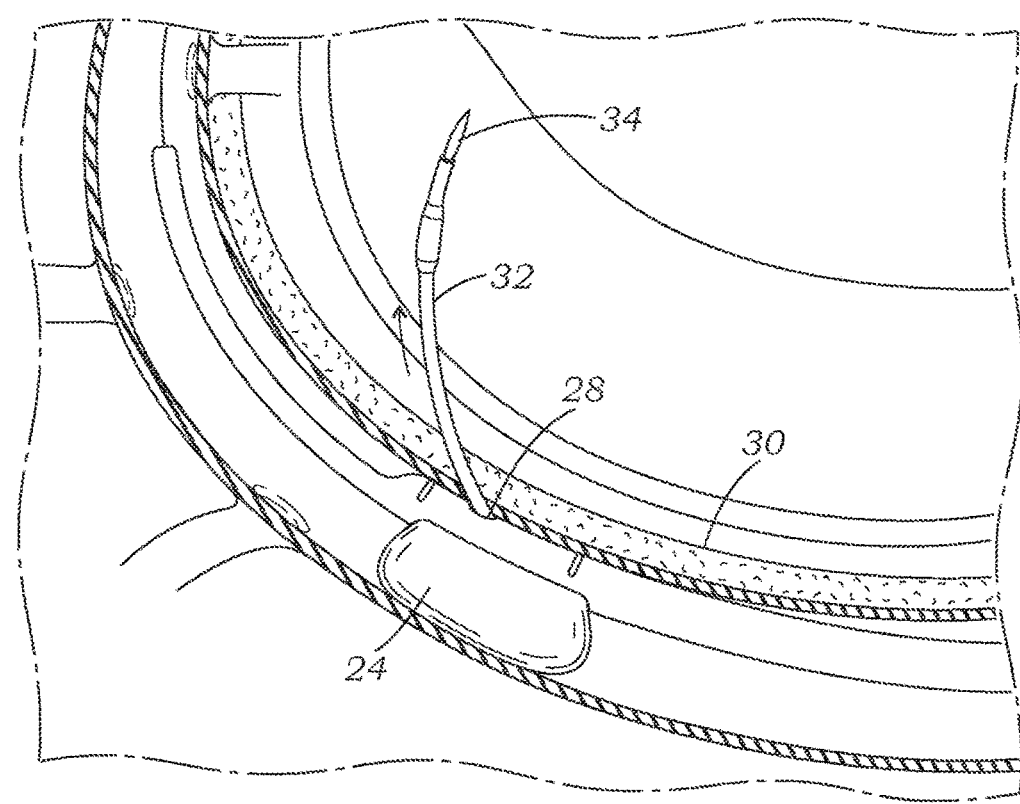

The curvature at the distal end of the puncture catheter 22 aligns to and "hugs" the anatomy within the coronary sinus and orients the needle port 28 inward, while the securing mechanism 24 holds the catheter 22 in place relative to the coronary sinus. Subsequently, as seen in FIG. 3D, a puncture sheath 32 having a puncture needle 34 with a sharp tip advances along the catheter 22 such that it exits the needle port 28 at an angle from the longitudinal direction of the catheter and punctures through the wall 30 into the left atrium. The puncture sheath 32 has a built-in curvature at the end that "aligns" with the curvature of the anatomy ensuring that the needle 34 is oriented inward toward the left atrium. The securing mechanism 24 provides rigidity to the system and holds the needle port 28 against the wall 30 (e.g., the securing mechanism 24 provides wall apposition). Preferably, the puncture needle 34 has a flattened configuration to form a linear incision and is mounted on the distal end of an elongated wire or flexible rod (not shown) that passes through a lumen of the puncture sheath 32.

Securing Mechanisms

Described herein are mechanisms for securing a catheter within a vessel to facilitate puncturing a wall of the vessel with a needle that extends from the catheter. The securing mechanisms described herein can be implemented in a catheter, such as the catheter 22 described herein with respect to FIGS. 3A-3D. Additionally, the securing mechanisms described herein are configured to provide the functionality of the generic securing mechanism 24 described herein with respect to FIGS. 3A-3D. In other words, the securing mechanisms described below can be used in place of the securing mechanism 24 and/or to provide the functionality of the securing mechanism 24, as described herein with respect to FIGS. 3A-3D.

The disclosed securing mechanisms are variations of the securing mechanism 24 that is used to secure the guidewire delivery catheter in place to facilitate puncturing the wall between the coronary sinus and the left atrium. The disclosed example securing mechanisms represent an improvement over other securing mechanisms, such as a saline-filled anchor balloon, because there is no risk of balloon burst and there is potential for better catheter securement. If the balloon bursts before the needle is deployed, the needle could deploy into the wrong space potentially causing severe damage to the patient. Moreover, a ruptured balloon could result in an embolism in the patient. The disclosed examples eliminate this risk. Furthermore, the disclosed examples eliminate the need to deflate the balloon, thereby providing a more streamlined puncturing procedure.

The disclosed securing mechanisms include mechanically releasing arms that are actuated to press against the coronary sinus wall to provide apposition for the guidewire delivery catheter, thereby ensuring that the needle punctures properly through the coronary sinus wall and into the left atrial space. The disclosed securing mechanisms comprise a compliant wire that extends outward from the catheter. The wire can be made from a shape memory material such as a nickel titanium alloy (e.g., Nitinol). The securing mechanisms can be activated by pushing the wire (e.g., at a proximal end of the catheter) to extend the securing mechanism out of the catheter. The securing mechanism can be configured to curve outward toward the coronary sinus wall. As the securing mechanism extends out of the catheter, the distal portion of the securing mechanism contacts the coronary sinus wall to secure the distal end of the catheter in place. The more the mechanically releasing arms are advanced, the closer the approach to the wall and the more force placed against the wall to anchor the catheter in place. The mechanically releasing arms can include a plurality of wires that angle or curve toward the vessel wall when deployed, one or more wires that coil away from the catheter to contact the vessel wall when deployed, or a stopper arm with a curved endcap that contacts the vessel wall when deployed. The securing mechanisms can extend from one side of the catheter or from a plurality of sides of the catheter.

The disclosed securing mechanisms are configured for use with a catheter, such as a guidewire delivery catheter. Disclosed herein are guidewire delivery catheters that have a securing mechanism (or anchor member) that includes one or more mechanically releasing arms. A first example securing mechanism includes two or more wires that advance out of a distal portion of the catheter to curve toward and contact the wall of the coronary sinus. A second example securing mechanism includes a wire that advances out of a distal portion of the catheter and coils toward and contacts the wall of the coronary sinus. A third example securing mechanism includes a wire that is advanced out of a distal portion of the catheter and includes a curved endcap at the end of the wire, the wire angled toward the wall of the coronary sinus.

Figures 4A, 4B, 4C, 4D:
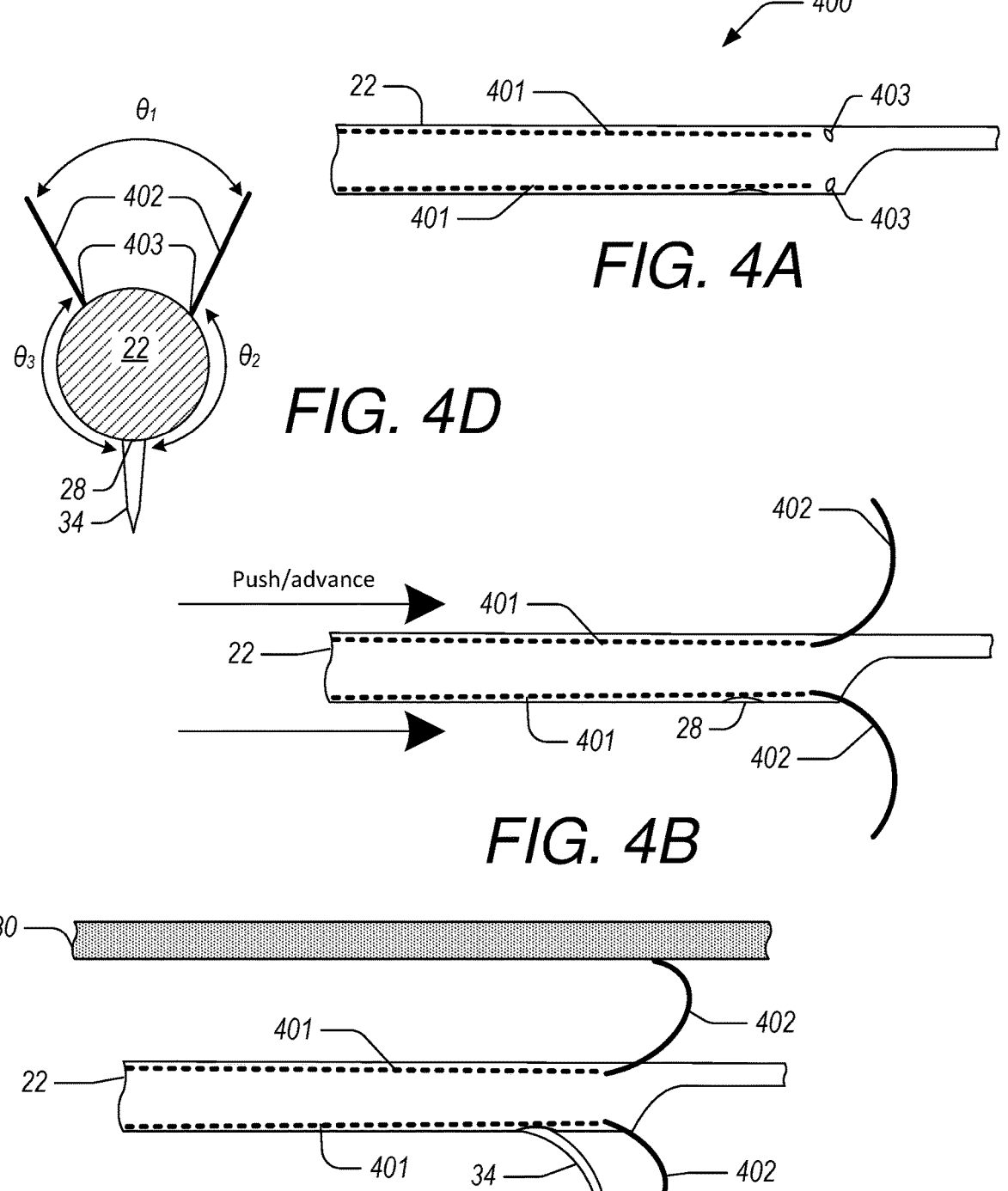
FIGS. 4A, 4B, 4C, and 4D illustrate a first example securing mechanism.

FIGS. 4A-4D illustrate a first example securing mechanism 400. The securing mechanism 400 includes two or more wires 401 housed along a length of the catheter 22 in a delivery configuration, as shown in FIG. 4A. The two or more wires 401 can be advanced out of a distal portion of the guidewire delivery catheter, at wire ports 403, to press against the wall of the coronary sinus to assume a deployment configuration, as shown in FIG. 4B. The securing mechanism 400 can be guided into place as part of the catheter 22 to where the needle 34 is to puncture the wall of the coronary sinus 30. Once in place, the wires 401 are pushed or advanced so that distal portions 402 of the wires 401 extend out of the distal portion of the catheter 22 and curve away from the catheter 22. Continued advancement of the wires 401 causes a distal portion 402 of each wire 401 to contact the wall of the coronary sinus 30, thereby securing the distal end of the guidewire delivery catheter 22 in place, as shown in FIG. 4C. The wires 401 can extend along a length of the catheter to a proximal portion of the catheter 22 to allow a user to advance the wires 401 from outside an operative site. FIGS. 4A-4C illustrate the wire ports 403 as being positioned distally to the needle port 28. However, it is to be understood that the wire ports 403 can be positioned proximally to the needle port 28 or approximately even with the needle port 28. Similarly, although the wire ports 403 are positioned at a same distal distance, it is to be understood that each wire port 403 can be positioned with different distal distances. The wires 401 can be pulled or withdrawn to retract the wires 401 into the catheter 22 to resume the delivery configuration.

The securing mechanism 400 material can be a compliant, wire material such as a nickel titanium alloy (e.g., Nitinol). In some examples, the distal portions 402 of the wires 401 can include protective material to reduce the likelihood that the distal portions 402 cause damage to the wall 30. In certain examples, the distal portions 402 of the wires 401 are curved to reduce the likelihood that the distal portions 402 cause damage to the wall 30.

FIG. 4C illustrates the wires 401 on opposite sides of the catheter 22 from one another. However, it is to be understood that the wires 401 can be positioned closer together, as shown in FIG. 4D. In addition, FIG. 4C illustrates the wires 401 such that one wire port 403 is on or near the same side of the catheter 22 as the needle port 28. In some instances, this may be undesirable due to the wire 401 on the same side of the needle 34 pushing the catheter 22 away from the wall 30 that is nearest the needle 34. Thus, in some examples, the wires 401 are configured so that the distal portions 402 of the wires push the wall 30 so that the resulting force is in a direction to provide wall apposition for the catheter 22 to push the catheter 22 against the wall 30 nearest the needle 34. In such examples, the wire ports 403 are positioned in a portion of the catheter 22 that is opposite to the portion of the catheter 22 that includes the needle port 28, an example of which is shown in FIG. 4D (which represents a cross-section of the catheter 22). For example, the azimuth angles θ2 and θ3 between the needle port 28 and the wire ports 403 can be at least 90 degrees and less than 180 degrees. It should be understood that reference to the azimuth angle is a reference to cylindrical coordinates, the azimuth angle measured within a cross-section of the catheter, the cross-section forming a surface perpendicular to a longitudinal axis of the catheter. In some examples, the azimuth angles θ2 and θ3 between the needle port 28 and the wire ports 403 can be at least 120 degrees. In some examples, the azimuth angle θ1 between the two wires 402 can be less than 180 degrees, between 0 degrees and 120 degrees, or between 5 degrees and 90 degrees. In some examples, the wire ports 403 are on a radially outer side of the catheter 22 while the needle port 28 is on a radially inner side of the catheter 22. Some example securing mechanisms 400 may include more than two wires and more than two corresponding wire ports. Such wire ports may be distributed on a radially outer side of the catheter 22 and/or may be distributed around the catheter 22.

Figure 5A:
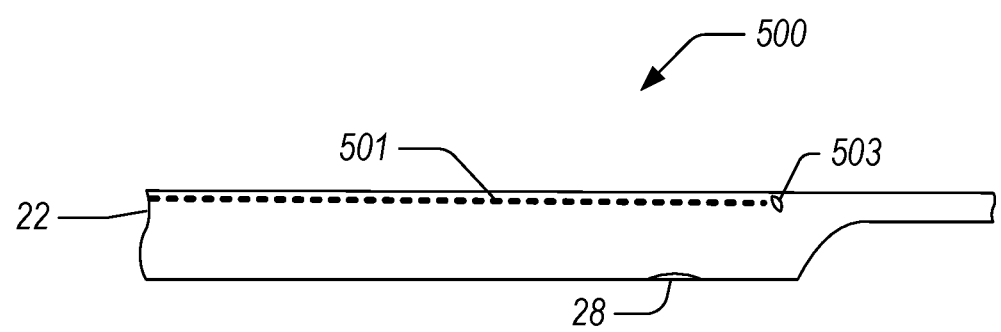
FIGS. 5A, 5B, and 5C illustrate a second example securing mechanism.
Figure 5B:
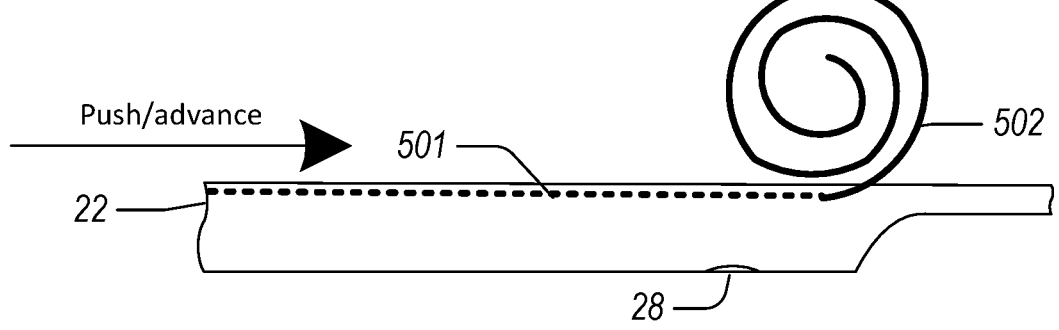
Figure 5C:
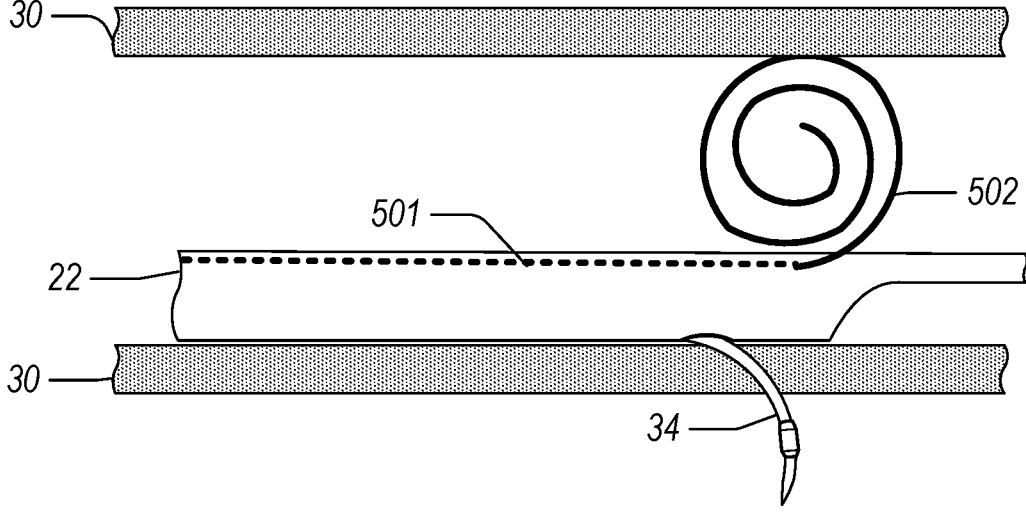

FIGS. 5A-5C illustrate a second example securing mechanism 500. The securing mechanism 500 can be a wire that advances out of a wire port 503 at a distal portion of the guidewire delivery catheter 22. In a delivery configuration, the wire 501 is housed within the catheter 22, as shown in FIG. 5A. As the wire 501 is advanced, a distal portion 502 of the wire 501 exits the wire port 503 and coils to assume a deployment configuration, as shown in FIG. 5B. The coiled distal portion 502 is configured to press against the wall of the coronary sinus 30, as shown in FIG. 5C. The securing mechanism 500 can be guided into place as part of the catheter 22 to where the needle 34 is to puncture the wall of the coronary sinus 30. Once in place, the wire 501 is pushed or advanced (e.g., from a proximal end of the catheter 22) so that a distal portion 502 of the wire 501 extends out of the wire port 503 of the catheter 22 and curves away from the catheter 22. Continued advancement of the wire 501 causes a distal portion 502 of the wire to coil and to contact the wall of the coronary sinus 30, thereby securing the distal end of the guidewire delivery catheter 22 in place. The wire 501 can extend along a length of the catheter to a proximal portion of the catheter 22 to allow a user to advance the wire 501 from outside an operative site. The material of the securing mechanism 500 can be a compliant, wire material such as a nickel titanium alloy (e.g., Nitinol). In some examples, the material can be shape set so that it coils upon exiting the wire port 503 to form the coil portion 502 of the wire 501. The wire 501 can be pulled or withdrawn to retract the wire 501 into the catheter 22 to resume the delivery configuration.

The wire port 503 is illustrated as being positioned distally to the needle port 28. However, it is to be understood that the wire port 503 can be positioned proximally to the needle port 28 or approximately even with the needle port 28. In addition, although a single wire 501 is illustrated, it is to be understood that a plurality of coiling wires can be used, with configurations similar to the securing mechanism 400 described with reference to FIGS. 4A-4D. As in the securing mechanism 400, the wire 501 (or at least the coiled portion 502 of the wire 501) can be coated with a material to reduce the risk of harming the vessel wall that it contacts.

Figure 6A:
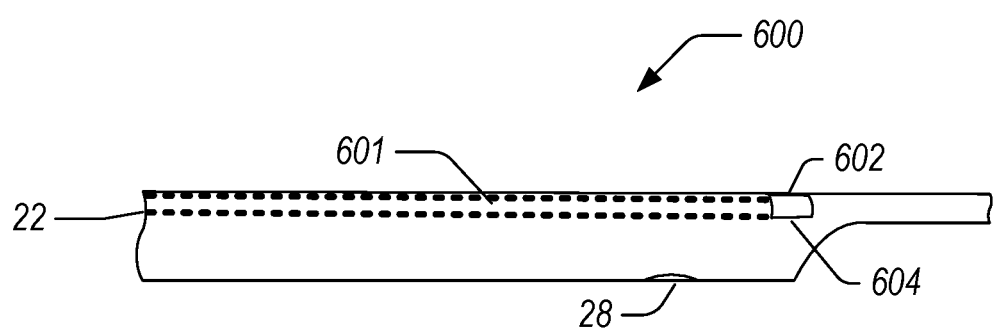
FIGS. 6A, 6B, and 6C illustrate a third example securing mechanism.
Figure 6B:
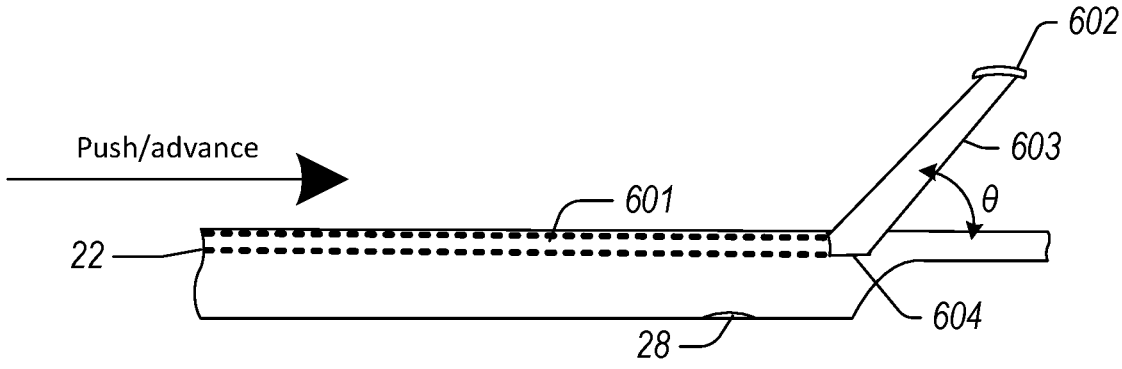
Figure 6C:
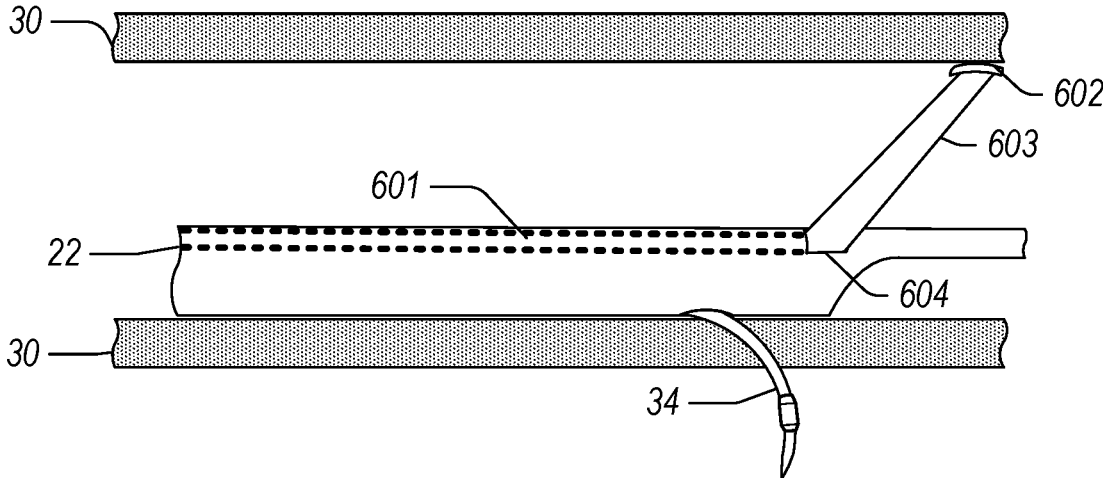

FIGS. 6A-6C illustrate a third example securing mechanism 600. The securing mechanism 600 can be a wire 601 that advances out of wire port 604 in a distal portion of the guidewire delivery catheter 22, as shown in FIG. 6A. The securing mechanism 600 includes a curved endcap 602 at a distal end of the wire 601. The curved endcap 602 acts to cover the wire port 604 in a delivery configuration, as shown in FIG. 6A. As such, the curved endcap 602 can be shaped to approximately follow a curvature of the catheter 22 at the wire port 604. As the wire 601 is advanced to change from the delivery configuration to the deployment configuration, a distal portion 603 of the wire 601 extends at an angle to the catheter 22, as shown in FIG. 6B. The securing mechanism 600 can be guided into place as part of the catheter 22 to where the needle 34 is to puncture the wall of the coronary sinus 30. Once in place, the wire 601 is pushed or advanced (e.g., from a proximal end of the catheter 22) so that a distal portion 603 of the wire 601 extends out of the wire port 604 to extend the curved endcap 602 towards the wall of the coronary sinus 30. Continued advancement of the wire 501 causes the curved endcap 602 to contact the wall of the coronary sinus 30, thereby securing the distal end of the guidewire delivery catheter in place, as shown in FIG. 6C. The curved endcap 602 can be configured to approximately follow the curvature of the wall of the coronary sinus 30. The wire 601 can be pulled or withdrawn to retract the wire 601 into the catheter 22 to resume the delivery configuration. When retracted, the curved endcap 602 can return to cover the wire port 604 to resume the delivery configuration.

The securing mechanism material can include a compliant, wire material such as a nickel titanium alloy (e.g., Nitinol). The wire 601 can be shape set so that it extends at a targeted angle from the catheter 22 as the wire is advanced out of the wire port 604. The angle, θ, the distal end of the wire 603 makes relative to the longitudinal axis of the catheter 22 can be less than or equal to about 90 degrees, and can be at least about 10 degrees and/or less than or equal to about 75 degrees, or at least about 30 degrees and/or less than or equal to about 60 degrees.

In some examples, the curved endcap 602 can include padding made of a material similar to the material of the outer portion of the catheter 22, such as a polyether block amide (e.g., PEBAX®). The curved endcap 602 can be sized to provide a surface area for a larger area of wall apposition.

The wire port 604 is illustrated as being positioned distally to the needle port 28. However, it is to be understood that the wire port 604 can be positioned proximally to the needle port 28 or approximately even with the needle port 28. In addition, although a single wire 601 is illustrated, it is to be understood that a plurality of wires with curved endcaps can be used, with configurations similar to the securing mechanism 400 described with reference to FIGS. 4A-4D.

Each of the securing mechanisms 400, 500, and 600 can include marker bands that are radio opaque to indicate a position of the securing mechanism, as visualized using fluoroscopy. In such examples, the marker bands can be opposite the needle 34 or needle port 28 to ensure that the needle 34 is located in a desirable position prior to extending the needle to puncture the wall 30.

ADDITIONAL EXAMPLES

Conditional language used herein, such as, among others, "can," "could," "might," "may," "e.g.," and the like, unless specifically stated otherwise, or otherwise understood within the context as used, is intended in its ordinary sense and is generally intended to convey that certain examples include, while other examples do not include, certain features, elements and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain examples require at least one of X, at least one of Y and at least one of Z to each be present.

It should be appreciated that in the above description of examples, various features are sometimes grouped together in a single example, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular example herein can be applied to or used with any other example(s). Further, no component, feature, step, or group of components, features, or steps are necessary or indispensable for each example. Thus, it is intended that the scope of the inventions herein disclosed and claimed below should not be limited by the particular examples described above but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example examples belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

Although certain preferred examples and examples are disclosed below, inventive subject matter extends beyond the specifically disclosed examples to other alternative examples and/or uses and to modifications and equivalents thereof. Thus, the scope of the claims that may arise herefrom is not limited by any of the particular examples described herein. The structures, systems, and/or devices described herein may be embodied as integrated components or as separate components. For purposes of comparing various examples, certain aspects and advantages of these examples are described. Not necessarily all such aspects or advantages are achieved by any particular example. Thus, for example, various examples may be carried out in a manner that achieves or optimizes one advantage or group of advantages as taught herein without necessarily achieving other aspects or advantages as may also be taught or suggested herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

Reference herein to "catheters," "tubes," "sheaths," "steerable sheaths," and/or "steerable catheters" can refer or apply generally to any type of elongate tubular delivery device comprising an inner lumen configured to slidably receive instrumentation, such as for positioning within an atrium or coronary sinus, including for example delivery catheters and/or cannulas.

What is claimed is:

1. A guidewire delivery catheter used to implant a shunt between the coronary sinus and the left atrium, the catheter comprising:

a needle housed within the catheter in a delivery configuration, the needle configured to extend out of the catheter to puncture a vessel wall in a deployment configuration;

a needle port through which the needle extends out of the catheter to transition from the delivery configuration to the deployment configuration;

a securing mechanism housed within the catheter in a delivery configuration, the securing mechanism comprising a compliant wire configured to be advanced out of the catheter in a deployment configuration; and a wire port through which the compliant wire of the securing mechanism extends out of the catheter to transition from the delivery configuration to the deployment configuration, wherein of the compliant wire of the securing mechanism is configured to form a coil with a plurality of loops exiting the wire port such that the coiled portion of the compliant wire is configured to come into contact with the vessel wall to provide wall apposition for the needle to puncture the vessel wall, wherein, in the deployment configuration, at least one of the plurality of loops is configured to come into contact with the vessel wall and a distal end of the compliant wire is configured to be spaced away from the vessel wall and to be outside of the guidewire delivery catheter.

2. The catheter of claim 1, wherein the compliant wire is configured to run along a length of the catheter such that the compliant wire is configured to be advanced by manipulating a component of the securing mechanism from outside of an operative site.

3. The catheter of claim 1, wherein the wire port is positioned opposite the needle port so that the compliant wire exits the catheter on an opposite side from where the needle exits the catheter.

4. The catheter of claim 1, wherein the wire port is positioned more distally along the catheter relative to the needle port.

5. The catheter of claim 1, wherein the wire port is positioned more proximally along the catheter relative to the needle port.

6. A guidewire delivery catheter used to implant a shunt between the coronary sinus and the left atrium, the catheter comprising:

a needle housed within the catheter in a delivery configuration, the needle configured to extend out of the catheter to puncture a vessel wall in a deployment configuration;

a needle port through which the needle extends out of the catheter to transition from the delivery configuration to the deployment configuration;

a securing mechanism housed within the catheter in a delivery configuration, the securing mechanism comprising a first compliant wire and a second compliant wire that are each configured to be advanced out of the catheter in a deployment configuration;

a first wire port through which the first compliant wire of the securing mechanism extends out of the catheter to transition from the delivery configuration to the deployment configuration, the first wire port positioned distally of the needle port so that a distal end of the first compliant wire exits the catheter distal to the needle port; and a second wire port through which the second compliant wire of the securing mechanism extends out of the catheter to transition from the delivery configuration to the deployment configuration, the second wire port positioned distally of the needle port so that a distal end of the second compliant wire exits the catheter distal to the needle port, wherein each of the first compliant wire and the second compliant wire are configured to form a coil with a plurality of loops, wherein a coiled portion of the first compliant wire and a coiled portion of the second compliant wire are configured to come into contact with the vessel wall to provide wall apposition for the needle to puncture the vessel wall while the distal end of the first compliant wire and the distal end of the second compliant wire are configured to be spaced away from the vessel wall and to be outside of the guidewire delivery catheter.

7. The catheter of claim 6, wherein, in a cross-section of the catheter, an azimuth angle between the needle port and each of the two wire ports is at least 90 degrees and less than 180 degrees.

8. The catheter of claim 6, wherein, in a cross-section of the catheter, an azimuth angle between the needle port and each of the two wire ports is at least 120 degrees.

9. The catheter of claim 6, wherein, in a cross-section of the catheter, an azimuth angle between the two wire ports is less than or equal to 120 degrees.

10. The catheter of claim 6, wherein the first compliant wire and the second compliant wire are each configured to run along a length of the catheter such that each of the first compliant wire and the second compliant wire is configured to be advanced by manipulating a component of the securing mechanism from outside of an operative site.

11. A guidewire delivery catheter used to implant a shunt between the coronary sinus and the left atrium, the catheter comprising:

a needle housed within the catheter in a delivery configuration, the needle configured to extend out of the catheter to puncture a vessel wall in a deployment configuration;

a needle port through which the needle extends out of the catheter to transition from the delivery configuration to the deployment configuration;

a securing mechanism housed within the catheter in a delivery configuration, the securing mechanism comprising a compliant wire configured to be advanced out of the catheter in a deployment configuration; and a wire port through which the compliant wire of the securing mechanism extends out of the catheter to transition from the delivery configuration to the deployment configuration, the wire port positioned distally of the needle port so that the compliant wire exits the catheter distal to the needle port, wherein the compliant wire includes a distal portion that extends from the wire port with a curved endcap at a distal end of the compliant wire so that the curved endcap of the compliant wire is configured to come into contact with the vessel wall to provide wall apposition for the needle to puncture the vessel wall, wherein the curved endcap is shaped to follow a curvature of a wall of the coronary sinus, wherein the curved endcap is shaped to follow a curvature of an outer surface of the guidewire delivery catheter at the wire port to cover the wire port in the delivery configuration.

12. The catheter of claim 11, wherein the compliant wire is shape set to exit the catheter at an exit angle.

13. The catheter of claim 11, wherein the compliant wire is configured to be advanced out of the catheter through the wire port by pushing a proximal portion of the compliant wire at a proximal end of the catheter.

14. The catheter of claim 11, wherein the compliant wire is configured to run along a length of the catheter such that the compliant wire is configured to be advanced by manipulating a component of the securing mechanism from outside of an operative site.

15. The catheter of claim 11, wherein the compliant wire comprises a shape memory metal.

16. The catheter of claim 11, wherein the curved endcap is coated with a material to reduce a likelihood of damaging the vessel wall.

17. The catheter of claim 11, wherein the wire port is positioned opposite the needle port so that the compliant wire exits the catheter on an opposite side from where the needle exits the catheter.

18. The catheter of claim 11, wherein the wire port is positioned more distally along the catheter relative to the needle port.

19. The catheter of claim 11, wherein the wire port is positioned more proximally along the catheter relative to the needle port.

* * * * *